United States Patent
van Engelen et al.

(10) Patent No.: US 9,643,147 B2
(45) Date of Patent: May 9, 2017

(54) STABILIZATION OF SUSPENDED SOLID PARTICLES AND/OR GAS BUBBLES IN AQUEOUS FLUIDS

(71) Applicant: Koninklijke Cooperatie Cosun U.A., Breda (NL)

(72) Inventors: Gerardus Petrus Franciscus Maria van Engelen, Bavel (NL); Gijsbert Adriaan van Ingen, Breda (NL); Corne Meeuwissen, Breda (NL); Robert Nolles, 's-Hertogenbosch (NL)

(73) Assignee: KONINKLIJKE COÖPERATIE COSUN U.A., Breda (NL)

( * ) Notice: Subject to any disclaimer, the term of this patent is extended or adjusted under 35 U.S.C. 154(b) by 0 days.

(21) Appl. No.: 14/776,371

(22) PCT Filed: Jan. 24, 2014

(86) PCT No.: PCT/NL2014/050037
§ 371 (c)(1),
(2) Date: Sep. 14, 2015

(87) PCT Pub. No.: WO2014/142651
PCT Pub. Date: Sep. 18, 2014

(65) Prior Publication Data
US 2016/0030907 A1    Feb. 4, 2016

(30) Foreign Application Priority Data

| Mar. 15, 2013 | (EP) | 13159522 |
| Apr. 22, 2013 | (EP) | 13164717 |
| Jul. 26, 2013 | (WO) | PCT/NL2013/050559 |
| Jul. 26, 2013 | (WO) | PCT/NL2013/050560 |
| Nov. 20, 2013 | (EP) | 13193699 |

(51) Int. Cl.

| B01J 13/00 | (2006.01) |
| C08H 8/00 | (2010.01) |
| C09K 8/20 | (2006.01) |
| C08L 1/02 | (2006.01) |
| D21C 5/00 | (2006.01) |
| D21C 9/00 | (2006.01) |
| D21H 11/12 | (2006.01) |
| D21H 11/18 | (2006.01) |
| D21H 15/02 | (2006.01) |
| C08B 37/00 | (2006.01) |
| C04B 28/04 | (2006.01) |

(Continued)

(52) U.S. Cl.
CPC .......... *B01J 13/0034* (2013.01); *C04B 16/02* (2013.01); *C04B 18/24* (2013.01); *C04B 28/04* (2013.01); *C08B 37/0003* (2013.01); *C08B 37/0045* (2013.01); *C08B 37/0057* (2013.01); *C08H 8/00* (2013.01); *C08L 1/02* (2013.01); *C09D 101/00* (2013.01); *C09K 8/206* (2013.01); *C11D 3/222* (2013.01); *C11D 17/0013* (2013.01); *C12P 19/14* (2013.01); *D21C 5/005* (2013.01); *D21C 9/002* (2013.01); *D21H 11/12* (2013.01); *D21H 11/18* (2013.01); *D21H 15/02* (2013.01); *C04B 2111/00103* (2013.01); *C04B 2111/00146* (2013.01); *C04B 2111/00482* (2013.01); *C08L 2205/02* (2013.01); *C08L 2205/16* (2013.01); *C08L 2205/18* (2013.01); *Y02W 30/97* (2015.05)

(58) Field of Classification Search
CPC ...... B01J 13/0034; C04B 16/02; C04B 28/04; C04B 2111/00103; C04B 2111/00146; C04B 2111/00482; C11D 17/0013; C11D 3/222; C09D 101/00; C12P 19/14; C08B 37/0045; C08B 37/0003; C08B 37/0057; D21C 9/002; D21C 5/005; C08H 8/00; D21H 11/12; D21H 11/18; D21H 15/02; C09K 8/206; C08L 1/02; C08L 2205/18; Y02W 30/97

See application file for complete search history.

(56) References Cited

U.S. PATENT DOCUMENTS

| 4,374,702 A | 2/1983 | Turbak et al. |
| 4,378,381 A | 3/1983 | Turbak et al. |

(Continued)

FOREIGN PATENT DOCUMENTS

| EP | 0 102 829 | 3/1984 |
| EP | 0 134 084 | 3/1985 |

(Continued)

OTHER PUBLICATIONS

Dinand, E., et al.; Cellulose, 1996, p. 183-188.*

(Continued)

*Primary Examiner* — Robert Jones, Jr.
(74) *Attorney, Agent, or Firm* — Gilberto M. Villacorta; Sunit Talapatra; Foley & Lardner LLP

(57) ABSTRACT

This invention relates to compositions that have utility, amongst others, in the stabilization of suspension particles or gas bubbles in fluid water-based compositions and/or in conferring shear thinning behavior to such fluid water-based compositions. The inventors have developed parenchymal cellulose based materials, which comprise cell wall derived networks of cellulose based fibers and nanofibrils, can advantageously be used for stabilization of suspended solid particles in fluid water-based compositions. Specific aspects of the invention concern the parenchymal cellulose based materials, their production and their use in fluid water-based compositions, as well as the resulting fluid water-based compositions per se.

19 Claims, 10 Drawing Sheets

(51) Int. Cl.
*C04B 18/24* (2006.01)
*C12P 19/14* (2006.01)
*C09D 101/00* (2006.01)
*C04B 16/02* (2006.01)
*C11D 3/22* (2006.01)
*C11D 17/00* (2006.01)
*C04B 111/00* (2006.01)

(56) References Cited

U.S. PATENT DOCUMENTS

| | | | |
|---|---|---|---|
| 4,629,575 A | 12/1986 | Weibel | |
| 4,831,127 A | 5/1989 | Weibel | |
| 4,923,981 A * | 5/1990 | Weibel | A21D 2/188 424/439 |
| 5,179,076 A | 1/1993 | Elward-Berry | |
| 5,252,352 A * | 10/1993 | Banach | A23C 9/1504 426/519 |
| 5,276,075 A | 1/1994 | Santini | |
| 5,567,462 A | 10/1996 | Ehrlich | |
| 5,656,734 A | 8/1997 | Ehrlich | |
| 5,964,983 A | 10/1999 | Dinand et al. | |
| 5,998,349 A | 12/1999 | Guillou | |
| 6,103,790 A | 8/2000 | Cavaille et al. | |
| 6,117,545 A | 9/2000 | Cavaille et al. | |
| 6,129,867 A | 10/2000 | Chevalier et al. | |
| 6,312,669 B1 | 11/2001 | Cantiani et al. | |
| 6,348,436 B1 | 2/2002 | Langlois et al. | |
| 6,703,497 B1 | 3/2004 | Ladouce et al. | |
| 6,967,027 B1 | 11/2005 | Heux et al. | |
| 7,705,084 B2 | 4/2010 | Van De Mark et al. | |
| 7,776,807 B2 | 8/2010 | Canto et al. | |
| 8,153,707 B2 | 4/2012 | Lynch et al. | |
| 2004/0086626 A1 | 5/2004 | Lundberg et al. | |
| 2005/0074542 A1 | 4/2005 | Lundberg et al. | |
| 2005/0256262 A1 | 11/2005 | Hill et al. | |
| 2006/0102869 A1 | 5/2006 | Cavaille et al. | |
| 2006/0289132 A1 | 12/2006 | Heijnesson-Hulten | |
| 2008/0108541 A1 | 5/2008 | Swazey | |
| 2008/0146485 A1 | 6/2008 | Swazey | |
| 2008/0146701 A1 | 6/2008 | Sain et al. | |
| 2009/0269376 A1 | 10/2009 | Lundberg et al. | |
| 2012/0142909 A1 | 6/2012 | Lundberg | |
| 2014/0124150 A1 | 5/2014 | Sabourin et al. | |
| 2015/0203737 A1 | 7/2015 | Van Engelen et al. | |
| 2015/0210957 A1 | 7/2015 | Napolitano | |

FOREIGN PATENT DOCUMENTS

| | | |
|---|---|---|
| JP | 2008-179666 A | 8/2008 |
| WO | WO 85/00402 A1 | 1/1985 |
| WO | WO-2009/101545 | 8/2009 |
| WO | WO-2010/105847 A1 | 9/2010 |
| WO | WO-2012/003307 A2 | 1/2012 |
| WO | WO-2012/052306 A1 | 4/2012 |
| WO | WO-2012/065924 | 5/2012 |
| WO | WO-2012/065925 | 5/2012 |
| WO | WO-2013128196 A1 | 9/2013 |

OTHER PUBLICATIONS

International Search Report issued in International Patent Application No. PCT/NL2014/050037 mailed Jul. 8, 2014.
European Search Report of EP 12178190 mailed Nov. 26, 2012.
International Search Report of PCT/NL2013/050558 mailed Aug. 29, 2013.
International Search Report of PCT/NL2013/050559 mailed Oct. 21, 2013.
International Search Report of PCT/NL2013/050560 mailed Oct. 15, 2013.
Machine translation of JP 2008-179666, 2016.

* cited by examiner

STABILIZATION OF SUSPENDED SOLID PARTICLES AND/OR GAS BUBBLES IN AQUEOUS FLUIDS

CROSS-REFERENCE TO RELATED APPLICATIONS

This application is the National Phase of International Patent Application No. PCT/NL2014/050037, filed Jan. 24, 2014, published on Sep. 18, 2014 as WO 2014/142651 A1, which claims priority to European Application No. 13159522.5, filed Mar. 15, 2013, European Application No. 13164717.4, filed Apr. 22, 2013, International Application No. PCT/NL2013/050560, filed Jul. 26, 2013, International Application No. PCT/2013/050559, filed Jul. 26, 2013, and European Application No. 13193699.9, filed Nov. 20, 2013. The contents of which are herein incorporated by reference in its entirety.

FIELD OF THE INVENTION

This invention relates to compositions that have utility, amongst others, in the stabilization of suspension particles and/or gas bubbles in fluid water-based compositions and/or in conferring shear thinning behavior to such fluid water-based compositions. Specific aspects of the invention concern the use of these compositions in fluid water-based compositions, as well as the resulting fluid water-based compositions per se.

BACKGROUND OF THE INVENTION

Suspensions are encountered in many types of industrial and/or consumer products, such as pharmaceutical products, alimentary products, detergent products, personal care products, paints and coatings, inks, fluid construction materials, agricultural products, etc.

A suspension, generally speaking, is a mixture of a liquid and a plurality of particles, typically of a solid material. Usually the suspension particles are larger than 1 micrometer in diameter (visible under a microscope). The size of the suspension particles typically results in the suspension being thermodynamically unstable; suspensions will settle over time if left undisturbed. This distinguishes a suspension from a colloid, in which the particles are smaller and do not settle.

It is generally understood that particle radius and rheology characteristics (of the continuous phase) have a bearing on suspension stability. This is expressed in the Stokes equation, which can be used to predict settling velocity, with continuous phase viscosity and particle radius as the main variables.

Similar considerations apply to the stabilization of gas bubbles suspended in a liquid, e.g. to produce a (low gas/liquid ratio) liquid foam, where gas bubble radius and rheology characteristics will determine whether the system is stable or whether the gas bubbles have a tendency for upward flotation, to eventually escape from the system.

It is known in the art to use additives for increasing the continuous phase viscosity in order to stabilize suspended solid particles or gas bubbles. To assure stability of such a system when it is left undisturbed additives have to be selected that confer a high viscosity at low or no shear, a property characterized by the zero-shear and/or low-shear viscosity. Some additives may confer a yield stress, meaning that a critical level of stress must be applied to initiate flow. The capability to stabilize suspended solid particles or gas bubbles in principle is characterized by the yield stress value and/or a sufficiently high zero-shear and/or a sufficiently high low-shear viscosity value.

An important factor in stabilization of suspended solid particles or gas bubbles is that it should not prohibit the product from flowing (without having to apply excessive forces), e.g. to extract it from a container or dispenser. Specific types of applications may require specific flow behavior. Ideally, for many applications, an additive for stabilization of suspended solid particles or gas bubbles should show shear thinning behavior, meaning that the viscosity is reduced when shear is increased to provide flowing behavior, while the viscosity at rest or at small disturbances can be high enough to stabilize the suspension. Shear thinning capabilities may be characterized by the pouring viscosity and the ratio of the pouring viscosity and low-stress viscosity values.

The ability of a certain structuring agent to provide shear thinning behavior alone is not necessarily sufficient to determine whether the liquid product is capable of suspending particles or gas bubbles with sufficient stability (and vice versa). For example, excessive amounts of additive may provide the required degree of stabilization but result in the liquid composition becoming overly viscous and non-pourable.

It is also common ground that stabilization benefits should be attained at as low a level of additive as possible for cost and formulation considerations, as is the case with any additive.

The development of additives that can stabilize systems comprising suspended particles or gas bubbles by retarding or preventing migration of the suspended solid particles or gas bubbles, without (negatively) affecting other properties of a formulation, in particular flow behavior, therefore remains technologically challenging.

Aiding to this challenge are current trends towards the use of bio-based ingredients, to reduce the environmental impact of the products in the broadest sense, and towards more concentrated products.

SUMMARY OF THE INVENTION

The inventors have developed parenchymal cellulose based materials, which comprise cell wall derived networks of cellulose based fibers and nanofibrils, can advantageously be used for stabilization of suspended solid particles or gas bubbles in fluid water-based compositions.

Without wishing to be bound by any particular theory, it is assumed that, in the cellulose particles of the invention, the organization of the cellulose fibrils as it exists in the parenchymal cell walls is at least partly retained, even though part of the pectin and hemicellulose is removed there from. Furthermore, the cellulose based nanofibrils are not completely unraveled, i.e. the material is not primarily based on completely unraveled nanofibrils, but instead can be considered to comprise, as the main constituent, parenchymal cell wall debris, having substantial parts of the pectin and hemicellulose removed. The inventors hypothesize that at least some hemicellulose and/or pectin is to be retained in the material to support the structural organization of the cellulose in the particles, e.g. by providing an additional network. Such hemicellulose networks would hold the cellulose fibers together, thereby providing structural integrity and strength to the cellulose particle.

The particulate cellulose material of this invention, is remarkably effective in preventing migration of suspended solid particles or gas bubbles, in particular the sedimentation of non-colloidal suspended particles, in water-based fluids and confers shear thinning behavior, so that the resulting products can still be made to flow e.g. under normal usage conditions.

Moreover, the particulate parenchymal cellulose material of this invention provides these (and other) advantageous properties in a broad range of products. The particulate cellulose product of the invention has been found to retain its functionality as a suspension stabilizing additive under harsh conditions, including high temperatures, at high and low pH values, at high ionic strength and/or in the presence of oxidizing and/or reducing agents. For example, test compositions structured with the materials of this invention and containing high concentrations of surfactant and/or high concentrations of electrolytes and/or high concentrations of HCl and/or oxidizing agents and/or significant enzyme activity still showed remarkable stability compared to many known structuring agents.

The particulate cellulose material of this invention is typically produced by subjecting parenchymal cell wall material to a process wherein part of the pectin and part of the hemicellulose is removed and the resulting material is subjected to shear so as to reduce the particle size to a certain extent. In the present invention, said parenchymal cell wall material can be derived from a variety of vegetable pulp materials. Particularly good results have been realized with particulate cellulose material produced from sugar beet pulp.

It has been found that the use of ensilaged sugar beet pulp in accordance with the invention confers particular advantageous. Ensilaging of sugar beet pulp typically involves conditions favorable to lactic acid fermentation resulting in lactic acid production and significant lowering of the pH. This beet pulp material is suitable for direct application in the process of the invention, using relatively mild chemical and mechanical treatment. Although the inventors do no wish to be bound by any particular theory, it is believed that the bonds between cells in the sugar beet pulp that has been ensilaged are weaker than without ensilaging so that moderate shearing is sufficient to separate the cells from one another whilst avoiding the formation of aggregates. This is advantageous in terms of process efficiency as well as product characteristics, which typically will be interrelated.

In accordance with the invention, materials may be utilized that, at present, are still mainly considered by-products in various industries, such as sugar refining industry. Turning such by-products into a new natural resource, is obviously considered an advantage at present times, with ever growing concerns about overuse and wasting of natural resources. The production of the present particulate cellulose material from these by-products, as will be described herein in greater detail, involves processing under generally mild conditions. As a result, also from a purely economical perspective, the material of this invention is quite attractive as a suspension stabilizing additive.

The particulate cellulose material of this invention can be provided in relatively concentrated forms, which are relatively easy to (re-)disperse into fluid water-based compositions. In particular it is not necessary to apply intensive processing steps in order to disperse the material. This is a significant advantage with a view to application of the material in highly concentrated products, where the addition of water together with the cellulose material is to be minimized.

These and other aspects of the invention will become apparent on the basis of the following detailed description and the appended examples.

DETAILED DESCRIPTION OF THE INVENTION

Figure 1A:
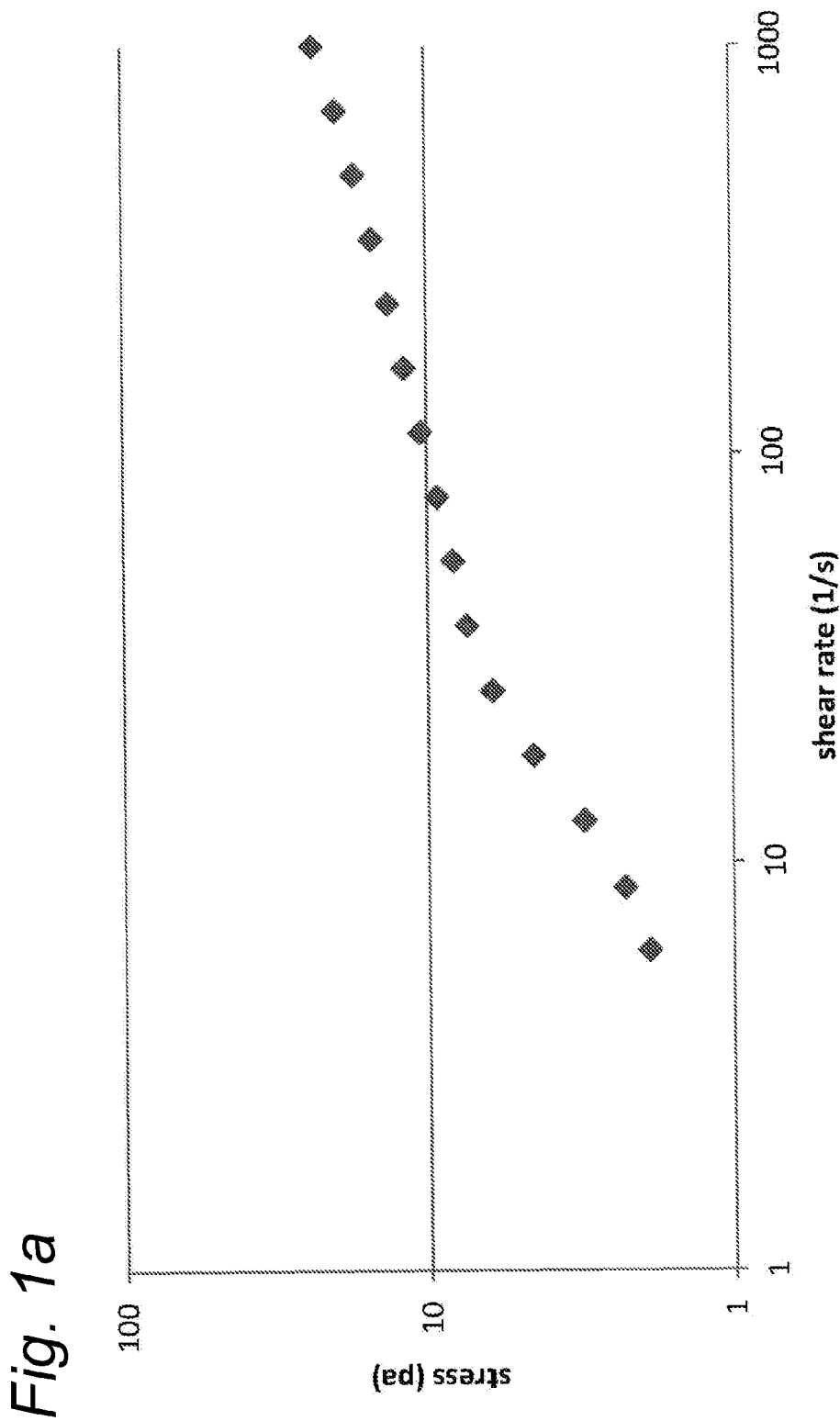
FIG. 1a shows the stress vs. shear rate profile of a 0.5% (w/w) MCF in water system.

Hence, a first aspect of the invention concerns the particulate cellulose material as defined herein per se, preferably a particulate cellulose material containing, by dry weight, at least 60% cellulose, 0.5-10% pectin and 1-15% hemicellulose, and has a volume-weighted median particle dimension within the range of 25-75 µm, preferably within the range of 35-65 µm, as measured by laser light diffractometry.

A further aspect of the invention concerns a method of producing a particulate cellulose material, as well as the particulate cellulose material obtainable by said method; the method comprising the steps of a) providing a parenchymal cell containing plant pulp, preferably a vegetable pulp, more preferably sugar beet pulp; b) subjecting the parenchymal cell containing plant pulp to chemical and/or enzymatic treatment resulting in partial degradation and/or extraction of pectin and hemicellulose; c) subjecting the material resulting from step b) to a high shear process whereby the particle size of the cellulose material is reduced so as to yield a particulate material having a volume-weighted median dimension within the range of 25-75 µm, as measured by laser diffractometry.

In a further aspect of the invention the use of the particulate cellulose material as defined herein is provided, for imparting shear thinning behavior in a fluid water-based composition.

In a further aspect of the invention, the use of the particulate cellulose material as defined herein is provided, for imparting thixotropic behavior in a fluid water-based composition.

In a further aspect of the invention, the use of the particulate cellulose material as defined herein is provided for imparting a high zero-shear viscosity in a fluid water-based composition, said high zero-shear viscosity being characterized by a value within the range of above $10^5$ mPa·s, preferably above $10^6$ mPa·s.

In a further aspect of the invention, the use of the particulate cellulose material as defined herein is provided for imparting a high low-shear viscosity in a fluid water-based composition, said high low-shear viscosity being characterized by a value of above $10^5$ mPa·s, preferably above $10^6$ mPa·s, at a shear rate within the range of $10^{-6}$-$10^{-1}$ s$^{-1}$ In a further aspect of the invention, the use of the particulate cellulose material as defined herein is provided for imparting a high yield-stress in a fluid water-based composition, said yield stress being characterized by a value within the range of 0.003-5.0 Pa.

In a further aspect of the invention, the use of the particulate cellulose material as defined herein is provided for stabilizing a non-colloidal particle fraction in a fluid water-based composition.

In a further aspect of the invention, the use of the particulate cellulose material as defined herein is provided for stabilizing suspended gas bubbles in a fluid water-based composition.

In yet a further aspect of the invention, a fluid water-based composition is provided comprising:
(a) an aqueous liquid or fluid;
(b) the particulate cellulose material as defined herein; and
(c) a non-colloidal particle fraction or gas bubbles,
wherein the fluid water-based composition is shear thinning and has a viscosity of above $10^5$ mPa·s, preferably above $10^6$ mPa·s, at a shear rate within the range of $10^{-6}$ to $10^{-1}$ s$^{-1}$.

In a further aspect of the invention, a method is provided for modifying the rheological characteristics of a fluid water-based composition, typically in order to achieve one or more of the above-recited effects, said method comprising incorporating in the fluid water-based composition the particulate cellulose material as defined herein.

Whenever, in this document, reference is made to the 'particulate cellulose material' this refers to the product as described herein on the basis of structural/chemical characteristics as well as to the products obtainable by the process described herein, which may be the same or different products, as will be understood by those skilled in the art, on the basis of the following. In particular, a property may be inherent to the materials obtained using the process described herein, without said property being described herein in an explicit way.

The particulate cellulose material of this invention is derived from parenchymal cell containing plant pulp. Parenchymal cell walls contain relatively thin cell walls (compared to secondary cell walls) which are tied together by pectin. Secondary cell walls are much thicker than parenchymal cells and are linked together with lignin. This terminology is well understood in the art. Polysaccharides typically can make up 90% or more of the primary plant cell walls, cellulose, hemicelluloses and pectins being the main constituents. The precise morphology and (chemical) make-up of parenchymal cell walls may vary considerably from species to species. The particulate cellulose material in accordance with the invention is preferably obtained from sugar beet, e.g. as a by-product of sucrose production.

The particulate cellulose material of this invention contains particles of specific structure, shape and size, as explained herein before. Typically the material contains particles having the form of platelets comprising parenchymal cellulose structures or networks. It is preferred that the size distribution of the particulate material falls within certain limits. When the distribution is measured with a laser light scattering particle size analyzer, such as the Malvern Mastersizer or another instrument of equal or better sensitivity, the diameter data is preferably reported as a volume distribution. Thus the reported median for a population of particles will be volume-weighted, with about one-half of the particles, on a volume basis, having diameters less than the median diameter for the population. Typically, the median major dimension of the particles of the parenchymal cellulose composition is within the range of 25-75 μm. More preferably the median major dimension of the particles of the parenchymal cellulose composition is within the range of 35-65 μm. Typically at least 90%, on a volume basis, of the particles has a diameter less than 120 μm, more preferably less than 110 μm, more preferably less than 100 μm. Typically at least 90%, on a volume basis, of the particles has a diameter above 5 μm, more preferably above 10 μm, more preferably above 25 μm. In an embodiment, the particulate cellulose material has a volume-weighted median minor dimension larger than 0.5 μm, preferably larger than 1 μm.

The term "cellulose" as used herein refers to homogeneous long chain polysaccharides comprised of β-D-glucose monomer units, of formula $(C_6H_{10}O_5)_n$, and derivatives thereof, usually found in plant cell walls in combination with lignin and any hemicellulose. The parenchymal cellulose of this invention may be obtained from a variety of plant sources containing parenchymal cell walls. Parenchymal cell wall, which may also be denoted as 'primary cell wall', refers to the soft or succulent tissue, which is the most abundant cell wall type in edible plants. Preferably the particulate cellulose material comprises, by dry weight, at least 60 wt %, preferably at least 70 wt %, more preferably at least 80 wt %, more preferably at least 90 wt % of cellulose.

The compositions of this invention are characterized by the fact that the majority of the cellulose material is present in the form of particles that are distinct from the nanofibrilised cellulose described in the prior art in that the cellulose nanofibrils are not substantially unraveled, as discussed before. Preferably, less than 10%, or more preferably less than 1% or less than 0.1% by dry weight of the cellulose within the composition is in the form of nanofibrillated cellulose. This is advantageous as nanofibrillated cellulose negatively affects the ability of the material to be processed and/or (re)dispersed. The term 'nanofibrils' refers to the fibrils making up the cellulose fibers, typically having a width in the nanometer range and a length of between up to 20 μm. It is to be noted that the nomenclature used in the field over the past decades has been somewhat inconsistent in that the terms 'microfibril' and 'nanofibril' have been used to denote the same material.

In accordance with the invention, the plant parenchymal cellulose material has been treated, modified and/or some components may have been removed but the cellulose has not substantially been broken down to individual nanofibrils, thereby substantially losing the structure of plant cell wall sections.

As mentioned before, the cellulose material of this invention has a reduced pectin content, as compared to the parenchymal cell wall material from which it is derived. Removal of some of the pectin is believed to result in enhanced thermal stability. The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the L-rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction.

It is preferred that the particulate cellulose material of the invention comprises less than 5 wt % of pectin, by dry weight of the particulate cellulose material, more preferably less than 2.5 wt %. The presence of at least some pectin in the cellulose material is nevertheless desired. Without wishing to be bound by any theory it is assumed that pectin plays a role in the electrostatic interactions between particles contained in the material and/or in supporting the network/structure of the cellulose. Additionally, the presence of some pectin might affect the capability of certain enzymes, e.g. those typically used in laundry detergent products, to degrade the cellulose in the material of the invention. Hence, it is preferred that the particulate cellulose material contains at least 0.5 wt % of pectin by dry weight of the particulate cellulose material, more preferably at least 1 wt %.

As mentioned before, the cellulose material of this invention has a certain minimum content of hemicellulose. The term "hemicellulose" refers to a class of plant cell-wall polysaccharides that can be any of several homo- or heteropolymers. Typical examples thereof include xylane, arabinane xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in molecular weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells. Without wishing to be bound by any theory, it is assumed that the presence of at least some hemicellulose is important to the structural organization of the fibers making up the particulate material. Additionally, the presence of some hemicellulose might affect the capability of certain enzymes, e.g. those typically used in laundry detergent products, to degrade the cellulose in the material of the invention. Preferably the particulate cellulose material comprises, by dry weight of the particulate cellulose material, 1-15 wt % hemicellulose, more preferably 1-10 wt % hemicellulose, most preferably 1-5 wt % hemicellulose.

Compositions containing the material of this invention, typically may take the form of an aqueous suspension or paste like 'additive', which can conveniently be dispersed in the fluid products in order to confer the desired rheological behavior. Embodiments are also envisaged wherein the parenchymal cellulose material of this invention is provided in powder form, which can be re-dispersed in fluid products. Composition containing the material of this invention typically can comprise other materials, as will be understood by those skilled in the art. Such other materials can include, e.g., remnants from (the processing of) the raw plant cell wall source (other than the particulate cellulose material of the invention) and any sort of additive, excipient, carrier material, etc., added with a view to the form, appearance and/or intended application of the composition.

A particulate cellulose material as described here above can be obtained using a specific process, which process involves a step of mild alkali treatment to hydrolyse the cell wall material followed by an intense homogenization process which does however not result in the complete unraveling of the material to its individual nanofibrils.

Accordingly, an aspect of the invention concerns a method of preparing a parenchymal cellulose composition as described in the foregoing, said method comprising the steps of;

a) providing a parenchymal cell containing plant pulp, preferably vegetable pulp, more preferably sugar beet pulp;
b) subjecting the parenchymal cell containing vegetable pulp to chemical and/or enzymatic treatment resulting in partial degradation and/or extraction of pectin and hemicellulose; and
c) subjecting the material resulting from step b) to a high shear process, wherein the particle size of the cellulose material is reduced so as to yield a particulate material having a volume-weighted median major dimension within the range of 25-75 μm, as measured by laser diffraction analysis;

According to an embodiment of the invention, said method comprising the steps of;

a) providing a parenchymal cell containing vegetable pulp;
b) subjecting the parenchymal cell containing vegetable pulp to chemical and/or enzymatic treatment resulting in partial degradation and/or extraction of pectin and hemicellulose, wherein the mixture may be homogenized once or several times by applying low shear force during and/or after said chemical and/or enzymatic treatment;
c) subjecting the material resulting from step b) to a high shear process, wherein the particle size of the cellulose material is reduced so as to yield a particulate material having a volume-weighted median major dimension within the range of 25-75 μm, as measured by laser diffraction analysis;
d) removing liquid from the mass obtained in step c).

As is known by those skilled in the art, in biology, the term "vegetable" means originating from and/or pertaining to any member of the plant kingdom and, in the context of this invention the terms 'vegetable pulp' and 'plant pulp' are deemed to be fully interchangeable. The parenchymal cell containing pulp used as the starting material typically comprises an aqueous slurry comprising ground and/or cut plant materials, which often can be derived from waste streams of other processes, in particular sugar beet pulp.

Particularly preferred is the use of fresh, pressed-out sugar beet pulp from which the sugars have been extracted and which has a dry solids content of 10-50 wt. %, preferably 20-30 wt. %, for example approximately 25 wt. %. Sugar beet pulp is the production residuum from the sugar beet industry. More specifically, sugar beet pulp is the residue from the sugar beet after the extraction of sucrose there from. Sugar beet processors usually dry the pulp. The dry sugar beet pulp can be referred to as "sugar beet shreds". Additionally, the dry sugar beet pulp or shreds can be formed and compressed to produce "sugar beet pellets". These materials may all be used as the starting material, in which case step a) will comprise suspending the dry sugar beet pulp material in an aqueous liquid, typically to the afore-mentioned dry solids contents. Preferably however, fresh wet sugar beet pulp is used as the staring material.

Another preferred starting material is ensilaged vegetable pulp, especially ensilaged sugar beet pulp. As used herein, the term "ensilage" refers to the process of storing vegetable materials in a moist state under conditions resulting in acidification caused by anaerobic fermentation of carbohydrates present in the materials being treated.

Ensilage is carried out according to known methods with pulps preferably containing 15 to 35% of dry matter. Ensilage of sugar beets is continued until the pH is within the range of 3.5-5. It is known that pressed beet pulps may be ensilaged to protect them from unwanted decomposition. This process is most commonly used to protect this perishable product, the other alternative being drying to 90% dry matter. This drying has the disadvantage of being very energy-intensive. The fermentation process starts spontaneously under anaerobic conditions with the lactic acid bacteria being inherently present. These microorganisms convert the residual sucrose of the pressed beet pulp to lactic acid, causing a fall in the pH. The storing of the sugar beet pulp under these conditions was found to confer specific characteristics that are advantageous with a view to the further processing of the material according to the method as defined herein and/or with a view of the characteristics of the material obtained accordingly.

Hence, in an embodiment of the invention, the method is provided, wherein step a) comprises providing ensilaged parenchymal cell containing vegetable pulp, preferably by:
a1) providing fresh parenchymal cell containing vegetable pulp, preferably fresh sugar beet pulp;
a2) if necessary adjusting the dry matter content of the fresh vegetable pulp to reach a value within the range of 15-35% (w/w);
a3) placing the vegetable pulp having a dry matter content of 15-35% in storage under conditions favorable to the growth of lactic acid producing bacteria; and
a4) keeping the material under said conditions favorable to the growth of lactic acid bacteria until the pH of the vegetable pulp has reached a value of below 5, preferably a value within the range of 3.5-5.

As is known by those of average skill in the art, common ensilaging practice results in the lactic acid fermentation as the required bacterial species are inherently present in the material. However, embodiments of the invention are envisaged wherein the vegetable pulp material is 'actively' inoculated with lactic acid producing bacteria. This would allow selecting specific strains. Conditions favorable to the growth of the lactic acid bacteria are known by those skilled in the art. In an embodiment of the invention, the process comprises placing the vegetable pulp in a silo or building a closely packed stack of the vegetable pulp and creating and maintaining an anaerobic environment during steps a3) and a4). Typically, the temperature of the vegetable pulp during steps a3) and a4) is not manipulated. Preferably steps a3) and a4) do not involve the application of external heat. In some embodiments measures may be applied in steps a3) and/or a4) to prevent excessive heating.

Other examples of vegetable pulps that may be employed in accordance with the present invention include, but are not limited to, pulps obtained from chicory, beet root, turnip, carrot, potato, citrus, apple, grape, or tomato, preferably pulps obtained from chicory, beet root, turnip, carrot or potato. Such pulps are typically obtained as side-streams in conventional processing of these vegetable materials. In one embodiment the use of potato pulp obtained after starch extraction is envisaged. In another embodiment of the invention, the use of potato peels, such as obtained in steam peeling of potatoes, is envisaged. In some embodiments, the use of press pulp obtained in the production of fruit juices is envisaged.

In an embodiment of the invention the parenchymal cell containing vegetable pulp is washed in a flotation washer before the chemical or enzymatic treatment of step b) is carried out, in order to remove sand and clay particles and, in case ensilaged sugar beet pulp is used as a starting material, in order to remove soluble acids.

The present inventors established that it is beneficial to subject the parenchymal cell containing plant pulp to treatment with an acid, in particular sulphuric acid. This step was found to have a number of highly advantageous effects. Most importantly, it was found that by applying this step, the material eventually obtained has improved visual appearance in that it is substantially more white, which is highly preferred, for obvious reasons, in many applications. In one embodiment of the invention, acid treatment of the plant pulp is performed and the process does not contain any further steps wherein the material is treated with a bleaching agent. In addition, the acid treatment of the plant pulp was found to allow for even milder treatment of the material in step b) of the present process. Although, the inventors do not wish to be bound by any particular theory, the acid treatment will result in the partial degradation and extraction of pectin. The acid treatment of the plant pulp also aids in the dissolving and removal or various salts from the material. Hence, in a preferred embodiment of the invention step a1) or a4) is followed by step a5), said step a5) comprising mixing the parenchymal cell containing pulp with an acid in an amount to lower the pH to below 4, preferably below 3, more preferably below 2. In a preferred embodiment, said acid is sulphuric acid. After addition of the acid, the mixture is preferably homogenized once or several times by applying low shear force, using e.g. conventional mixers or blenders. Preferably, the step of homogenization at low shear is carried out for at least 5 minutes, preferably at least 10 minutes, preferably at least 20 minutes. In an embodiment, this acid treatment is followed by a step of removing at least part of the water. In one preferred embodiment of the invention this may be accomplished using filtration, e.g. in a chamber filter press. As will be understood by those skilled in the art, it is possible to incorporate multiple wash cycles to achieve optimal results. The implementation of this step a5) beneficially affects the material obtained by the process of this invention, amongst others, in that it significantly improves the visual appearance thereof, as will be illustrated in one of the appending examples.

In accordance with the invention, the chemical and/or enzymatic treatment of step b) results in the degradation and/or extraction of at least a part of the pectin and hemicelluloses present in the parenchymal cell containing vegetable pulp, typically to monosaccharides, disaccharides and/or oligosaccharides, typically containing three to ten covalently bound monosaccharides. However, as indicated above, the presence of at least some pectin, such as at least 0.5 wt %, and some hemicellulose, such as 1-15 wt %, is preferred. As will be understood by those skilled in the art, said pectin and hemicellulose remaining in the cellulose material can be non-degraded and/or partially degraded. Hence, step b) typically comprises partial degradation and extraction of the pectin and hemicellulose, preferably to the extent that at least 0.5 wt. % of pectin and at least 1 wt. % of hemicellulose remain in the material. It is within the routine capabilities of those skilled in the art to determine the proper combinations of reaction conditions and time to accomplish this.

Preferably, the chemical treatment as mentioned in step b) of the above mentioned method comprises:

b1) mixing the parenchymal cell containing vegetable pulp with alkaline metal hydroxide to a final concentration of 0.1-1.0 M, preferably 0.3-0.7 M; and b2) heating the mixture of parenchymal cell containing vegetable pulp and alkaline metal hydroxide to a temperature within the range of 80-120° C. for a period of at least 10 minutes, preferably at least 20 minutes, more preferably at least 30 minutes.

It has been found that the use of alkaline metal hydroxides, especially sodium hydroxide, in the above method, is advantageous to efficiently remove pectin and hemicelluloses from the cellulose. The alkaline metal hydroxide may be sodium hydroxide. The alkaline metal hydroxide may be potassium hydroxide. The alkaline metal hydroxide may be mixed with the parenchymal cell containing vegetable pulp to a concentration of at least 0.1 M, at least 0.2 M, at least 0.3 M, or at least 0.4 M. The alkaline metal hydroxide concentration preferably is at less than 0.9 M, less than 0.8 M, less than 0.7 M or less than 0.6 M.

The use of relatively low temperatures in the present chemical process allows the vegetable material pulp to be processed with the use of less energy and therefore at a lower cost than methods known in the art employing higher temperatures. In addition, use of low temperatures and pressures ensures that minimum cellulose nanofibers are produced. Cellulose nanofibers affect the viscosity of the composition and make it more difficult to rehydrate and/or redisperse the composition after dehydration or concentration. The vegetable material pulp may be heated to at least 80° C. Preferably, the vegetable material pulp is heated to at least 90° C. Preferably, the vegetable material pulp is heated to less than 120° C., preferably less than 100° C. As will be appreciated by those skilled in the art, the use of higher temperatures, within the indicated ranges, will reduce the processing times and vice versa. It is a matter of routine optimization to find the proper set of conditions in a given situation. As mentioned above, the heating temperature is typically in the range of 80-120° C. for at least 10 minutes, preferably at least 20 minutes, more preferably at least 30 minutes. If the heating temperature in step b2) is between 80-100° C., the heating time may be at least 60 minutes. Preferably, step b2) comprises heating the mixture to a temperature of 90-100° C. for 60-120 minutes, for example to a temperature of approximately 95° C. for 120 minutes. In another embodiment of the invention, the mixture is heated above 100° C., in which case the heating time can be considerably shorter. In a preferred embodiment of the present invention step b2) comprises heating the mixture to a temperature of 110-120° C. for 10-50 minutes, preferably 10-30 minutes.

Preferably the chemical or enzymatic treatment is followed by a step of removing at least part of the water, with the aim of removing a substantial fraction of dissolved and/or dispersed matter. In one preferred embodiment of the invention, the mass may be subjected to filtration, e.g. in a chamber filter press. As will be understood by those skilled in the art, it is possible to incorporate multiple processing steps in order to achieve optimal results. For example, an embodiment is envisaged wherein the mixture is filtered, followed by the addition of water or liquid followed by an additional step of removal of liquid, e.g. using a chamber filter press, to result in an additional washing cycle. This step may be repeated as many times as desired in order to achieve a higher degree of purity.

In an embodiment of the invention, at least a part of the pectin and hemicelluloses may be degraded by treatment of the vegetable pulp with suitable enzymes. Preferably, a combination of enzymes is used, although it may also be possible to enrich the enzyme preparation with one or more specific enzymes to get an optimum result. Generally an enzyme combination is used with a low cellulase activity relative to the pectinolytic and hemicellulolytic activity. In a preferred embodiment of the present invention such a combination of enzymes, has the following activities, expressed as percentage of the total activity of the combination:

cellulase activity of 0-10%;
pectinolytic activity of 50-80%; and
hemicellulase activity of at least 20-40%

The enzyme treatments are generally carried out under mild conditions, e.g. at pH 3.5-5 and at 35-50° C., typically for 16-48 hours, using an enzyme activity of e.g. 65.000-150.000 units/kg substrate (dry matter). It is within the routine capabilities of those skilled in the art to determine the proper combinations of parameters to accomplish the desired rate and extent of pectin and hemicellulose degradation.

Before, during or after step b) the mixture is preferably homogenized once or several times by applying low shear force. Low shear force can be applied using standard methods and equipment known to those skilled in the art, such as conventional mixers or blenders. Preferably, the step of homogenisation at low shear is carried out for at least 5 minutes, preferably at least 10 minutes, preferably at least 20 minutes.

The present inventors established that it is beneficial to subject the mass resulting from step b) to treatment with an acid, in particular sulphuric acid. This step typically is performed to dissolve and optionally remove various salts from the material, but it may affect the material in different ways as well. Hence, in a preferred, the treatment of step b) of the present method additionally comprises the additional step b3) of mixing the treated parenchymal cell containing pulp with an acid in an amount to lower the pH to below 4, preferably below 3, more preferably below 2. In a preferred embodiment, said acid is sulphuric acid. After addition of the acid, the mixture is preferably homogenized once or several times by applying low shear force, using e.g. conventional mixers or blenders. Preferably, the step of homogenisation at low shear is carried out for at least 5 minutes, preferably at least 10 minutes, preferably at least 20 minutes. Typically, the process of this invention will only include one acid treatment step, i.e. it will not include the step b3) if the acid treatment step a5)' is implemented.

Step c) typically involves high shear treatment of the mass resulting from step b), which will typically result in cellulose platelets being e.g. less than half the size of the parent cells, preferably less than one third the size of the parent cells. As mentioned before, the inventors have found that it is important to retain part of the structure in the cellulose particles to ensure that the composition provides the advantageous characteristics described herein. As will be understood from the foregoing, the processing during step d) should not result in the complete or substantial unraveling to nanofibrils.

The process of obtaining the desired particle size characteristics of the cellulose material in step c) is not particularly limited and many suitable methods are known to those skilled in the art. Examples of suitable size reducing techniques include grinding, crushing or microfluidization. Suitably the process is conducted as wet processes, typically by subjecting the aqueous liquid from step b), which may e.g. contain 1 to 50% cellulosic material, to grinding, crushing, microfluidization or the like.

Most preferred examples of high shear equipment for use in step c) include friction grinders, such as the Masuko supermasscolloider; high pressure homogenizers, such as a Gaulin homogeninizer, high shear mixers, such as the Silverson type FX; in line homogenizer, such as the Silverson or Supraton in line homogenizer; and microfluidizers. The use of this equipment in order to obtain the particle properties required by this invention is a matter of routine for those skilled in the art. The methods described here above may be used alone or in combination to accomplish the desired size reduction.

In a preferred embodiment of the invention, heating is discontinued after step b) and the mass may be allowed to cool in between steps b) and c) or it may be transferred to the homogenizer directly, where no additional heating takes place. In a preferred embodiment step c) is performed while the material is at ambient temperature. In another preferred embodiment of the invention step c) is performed while the material is at above-ambient temperature, e.g. at temperatures of up to 80° C. In one embodiment of the invention, step c) is performed at a temperature within the range of 60-80° C.

Preferably, after the step of reducing the particle size of the cellulose, a separation on the basis of particle size is carried out. Examples of useful separation techniques are sieve classification, membrane filtration and separations using a cyclone or centrifuge.

The aim of the removal of water during step d) is primarily to remove a substantial fraction of dissolved organic material as well as a fraction of unwanted dispersed organic matter, i.e. having a particle size well below the particle size range of the particulate cellulose material.

In view of the first objective, it is preferred not to use methods relying on evaporation, as will be understood, since this will not remove any of the dissolved salts, pectin, proteins, etc., which are exactly the components to be washed out by this step. Preferably, step d) does not comprise a drying step, such as evaporation, vacuum drying, freeze-drying, spray-drying, etc. In one preferred embodiment of the invention, the mass may be subjected to microfiltration, dialysis, centrifuge decantation or pressing.

As will be understood by those skilled in the art, it is possible to incorporate multiple processing steps in order to achieve optimal results. For example, an embodiment is envisaged wherein step d) comprises subjecting the mixture to microfiltration, dialysis or centrifuge decantation, or the like, followed by a step of pressing the composition.

As will be understood by those skilled in the art, step d) may also comprise the subsequent addition of water or liquid followed by an additional step of removal of liquid, e.g. using the above described methods, to result in an additional washing cycle. This step may be repeated as many times as desired in order to achieve a higher degree of purity.

Preferably, following step d), the composition is added to an aqueous medium and the cellulose particles within the composition are rehydrated and uniformly suspended within the aqueous medium, preferably under (low shear) mixing. Rehydration under low shear mixing ensures that the energy cost to rehydrate is low and that the cellulose platelets are not damaged, or that a significant proportion of the cellulose platelets are not damaged during the mixing process.

In a preferred embodiment of the invention, step d) is performed while the material is at ambient temperature. In another preferred embodiment of the invention step d) is performed while the material is at above-ambient temperature, e.g. at temperatures of up to 85° C. In one embodiment of the invention, step d) is performed at a temperature within the range of 60-85° C.

Once compositions comprising the particulate cellulose material have been produced, it is often desirable to increase the concentration of the cellulose material to reduce the volume of the composition and thereby e.g. reduce storage and transport costs. Accordingly, the composition of cellulose platelets may be concentrated, e.g. to at least 5 wt % solids, preferably at least 10 wt % solids, that may be added in small quantities to the fluid products to confer the desired structuring properties.

The present invention concerns the use of the particulate cellulose material as defined in the foregoing and/or as obtainable by any of the methods described in the foregoing for modifying a fluid water-based composition, said use typically comprising incorporating said particulate cellulose material in said fluid water-based composition.

The present invention also concerns the fluid water-based compositions wherein the particulate cellulose material as defined in the foregoing and/or as obtainable by any of the methods described in the foregoing has been incorporated.

The present invention, in another aspect concerns a method of modifying a fluid water-based composition comprising incorporating in a fluid water-based composition a particulate cellulose material as defined in the foregoing and/or as obtainable by any of the methods described in the foregoing.

Incorporation of the particulate cellulose material is envisaged in a very broad range of fluid water-based compositions, especially those where both suspension stability and pourability and/or flowability are factors of interest.

Examples of such fluid water-based compositions include products selected from the group consisting of pharmaceutical products, detergent products, personal care products, alimentary products, concrete, paints/coatings, well drilling fluids, inks, crop protection products, spray-plaster, mortar, etc.

In a preferred embodiment of the invention, a fluid water-based composition is provided comprising (a) an aqueous liquid or fluid; (b) 0.01-2.5% (w/w) of the particulate cellulose material; and (c) 0.5-70% (w/w) of a non-colloidal particle fraction, wherein said non-colloidal particle fraction does not include the particulate cellulose material.

As used herein the term "fluid water based composition" encompasses water based compositions that exhibit a fluid or flowable characteristic, such as a liquid, a paste, etc. Matter exhibiting solid like behaviour below the yield stress and fluid-like behaviour beyond the yield stress is also encompassed by the term "fluid water based composition".

Advantageously, the fluid water-based composition comprises at least 0.05% (w/w), more preferably at least 0.075% (w/w), more preferably at least 0.1% (w/w), more preferably at least 0.125% (w/w), more preferably at least 0.15% (w/w), more preferably at least 0.175% (w/w), more preferably at least 0.2% (w/w) of the particulate cellulose material. Advantageously, the fluid water-based composition of the invention comprises up to 3.0% (w/w), more preferably up to 2.5% (w/w), more preferably up to 2.0% (w/w), more preferably up to 1.5% (w/w), more preferably up to 1.25% (w/w), more preferably up to 1.0% (w/w), more preferably up to 0.75% (w/w) of the particulate cellulose material. The most preferred level is within the range of 0.3-0.6% (w/w).

The ability of the fluid water-based compositions of the invention to keep non-colloidal particles in suspension, in one embodiment, correlates with the yield stress value. Typically, in order to stabilize non-colloidal particles in the fluid water-based compositions, the stress applied by one single particle must not exceed the yield stress value of the liquid matrix. If this condition is fulfilled the composition will be less susceptible to migration of the non-colloidal particles (sedimentation or settling) or the suspended gas bubbles (upward flotation) under static conditions. The particulate cellulose material is preferably applied in the fluid water-based compositions in accordance with the present invention to produce a yield stress within the range of 0.003-5.0 Pa, preferably within the range of 0.01-1.0 Pa, more preferably within the range of 0.05-0.2 Pa.

The incorporation of the particulate cellulose material in the fluid water-based compositions in accordance with the present invention preferably results in the fluid water-based composition becoming shear thinning. Shear thinning, as used herein, means that the fluid's resistance to flow decreases with an increase in applied shear stress. Shear thinning is also referred to in the art as pseudoplastic behavior. Shear thinning can be quantified by the so called "shear thinning factor" (SF) which is obtained as the ratio of viscosity at 1 s$^{-1}$ and at 10 s$^{-1}$: A shear thinning factor below zero (SF<0) indicates shear thickening, a shear thinning factor of zero (SF=0) indicates Newtonian behavior and a shear thinning factor above zero (SF>0) stands for shear thinning behavior. In an embodiment of the invention the shear thinning property is characterized by the liquid matrix having a specific pouring viscosity, a specific low-stress viscosity, and a specific ratio of these two viscosity values.

The pouring viscosity, as defined herein, is measured at a shear rate of 20 s$^{-1}$. In a preferred embodiment of the invention, a pouring viscosity is attained ranging from 50 to 2500 mPa·s, preferably from 100 to 1500 mPa·s.

The low-shear viscosity, as defined herein, is determined under a constant low-stress of 0.1 Pa. The incorporation of the particulate cellulose material in the fluid water-based compositions in accordance with the present invention typically results in a low-stress viscosity of at least $10^4$ mPa·s, preferably at least $10^5$ mPa·s, and preferably at least $10^6$ mPa·s.

The zero-shear viscosity is a not a direct measurement but a calculus or extrapolation from measurements at lower shear rate values. In one embodiment, the incorporation of the particulate cellulose material in the fluid water-based compositions in accordance with the present invention typically results in a zero-stress viscosity of at least $10^4$ mPa·s, preferably at least $10^5$ mPa·s, and preferably at least $10^6$ mPa·s.

To exhibit suitable shear-thinning characteristics, in one embodiment, the incorporation of the particulate cellulose material in the fluid water-based compositions in accordance with the present invention typically results in a ratio of low-stress viscosity to pouring viscosity value, which is at least 2, preferably at least 10, preferably at least 100, up to 1000 or 2000.

The incorporation of the particulate cellulose material in the fluid water-based compositions in accordance with the present invention typically results in the fluid water-based composition becoming thixotropic. Thixotropy is a shear thinning property. Thixotropic compositions show shear thinning over time when a stress is applied and need some time to return to the more viscous state when the stress is removed. Thixotropic materials are characterized by a hysteresis loop. The hysteresis loop is flow curve, obtained by measurements on a viscometer, showing for each value of rate of shear, two values of shearing stress, one for an increasing rate of shear and the other for a decreasing rate of shear. Hence, the "up curve" and "down curve" do not coincide. This phenomenon is caused by the decrease in the fluid's viscosity with increasing time of shearing. Such effects may or may not be reversible; some thixotropic fluids, if allowed to stand undisturbed for a while, will regain their initial viscosity, while others never will. The present inventors established that the fluid water-based compositions of this invention are characterized by complete and relatively fast recovery of the initial viscosity. Typically, the "up curve" and "down curve" are relatively close and the "up" curves" as well as the "down curves" of subsequent measurement cycles will coincide completely or nearly completely. As will be understood by those skilled in the art, this capability to regain initial viscosity quickly and completely is a particular advantage, with a view to preventing sedimentation of non-colloidal particles in suspensions, e.g. when, during use of the product, a portion of the product is to be extracted from the container with the application of shear. Hence, in an embodiment of the invention, the use of the particulate cellulose material is provided for imparting shear-thinning and/or thixotropic behaviour in a fluid water-based composition with enhanced capabilities to regain initial viscosity after the application of shear.

Also, in one embodiment, the incorporation of the particulate cellulose material in the fluid water-based compositions in accordance with the present invention typically results in a stress v. shear rate profile with a slope of at least 0.05, preferably at least 0.1, more preferably at least 0.2, at least 0.3, at least 0.4 or at least 0.5. The incorporation of the particulate cellulose material in the fluid water-based compositions in accordance with the present invention furthermore typically results in a stress v. shear rate profile with a slope of below 1.5, preferably below 1, more preferably below 0.9, below 0.8, below 0.7, below 0.6 or below 0.5. More in particular, a stress v. shear rate profile is attained with a slope of >0, preferably of at least 0.05, preferably at least 0.1, more preferably at least 0.2, at least 0.3, at least 0.4 or at least 0.5, within the shear rate range of from 1 to 1000 s$^{-1}$, more preferably of 10 to 1000 s$^{-1}$, more preferably form 10 to 100 s$^{-1}$. As will be understood by those skilled in the art on the basis of the information mentioned herein, the >0 slope typically means that the product has sufficient flow stability and is less prone to shear banding and lumpiness.

Unless indicated otherwise, viscosity and flow behavior measurements, in accordance with this invention, are performed using a Haake model VT550 viscometer (spindle MV1), at 1 to 1000 s$^{-1}$ and conducted at 25° C.

Rheology parameters defined herein concern the combination of the aqueous liquid or fluid and the particulate cellulose material. The presence of suspended particles can influence yield stress measurements. The above-defined preferred values can typically be attained with systems comprising the particulate cellulose material of this invention at a level within the range of 0.3-0.6% (w/w), but the scope of the invention is not limited to such levels, as will be understood by those skilled in the art. Yet, in particularly preferred embodiments of the invention, the uses and methods of this invention involve the incorporation of the particulate cellulose material at a level within the range of 0.3-0.6% (w/w).

The term "aqueous liquid or fluid" is used herein to generally refer to the liquid or fluid matrix containing the particulate cellulose material and further non-colloidal suspended particle fraction, which contains a liquid continuous phase with water as the main solvent. Besides water, the aqueous liquid or fluid can contain significant amounts of solutes, other solvents and/or colloidal components dispersed within the continuous aqueous phase, as will be appreciated by those skilled in the art. In an embodiment, the aqueous liquid or fluid comprises water in an amount of at least 50% (w/w), more preferably at least 60% (w/w), more preferably at least 70% (w/w), more preferably at least 80% (w/w), more preferably at least 90% (w/w). Embodiments are however also envisaged, wherein the aqueous liquid or fluid comprises water in amounts of only 5% (w/w) or more, e.g. in combination with other water-miscible solvents such as ethanol.

In an embodiment, the fluid water-based composition comprises water in an amount of at least 10% (w/w), more preferably at least 20% (w/w), more preferably at least 25% (w/w), more preferably at least 30% (w/w). Furthermore, In an embodiment, the fluid water-based composition of the invention comprises water in an amount of less than 85% (w/w), more preferably less than 75% (w/w), more preferably less than 70% (w/w), more preferably less than 60% (w/w), more preferably less than 50% (w/w), more preferably less than 40% (w/w), more preferably less than 35% (w/w). In certain embodiments the fluid water-based composition is a concentrated formulation comprising as low as 1 to 30% (w/w) water, e.g. from 5 to 15% (w/w), preferably from 10 to 14% (w/w).

It has been found that the particulate cellulose material is capable of providing the desired structuring benefits at pH values within the entire range of 1-14. It has importantly been found that the particulate cellulose material is capable of providing the desired structuring benefits at extremely low pH values, which is a particular advantage of the present invention. In preferred embodiment, therefore, the aqueous liquid or fluid has a pH of below 6, below 5, below 4, below 3, or below 2

The aqueous medium may comprise any amount of dissolved components. It will be understood by those skilled in the art that a wide variety of such components may suitably be included in the fluid water-based compositions and in a wide range of concentrations, the exact preferences depending entirely on the type of product to be constituted by the fluid water-based composition. Interestingly, the present inventors have established that the particulate cellulose material of this invention is able to retain most of its favourable rheology characteristics in the presence of high levels of electrolytes, at a wide range of pH values and/or in the presence of oxidizing and/or reducing agents.

The aqueous medium may additionally comprise one or more colloidal components, so that the aqueous liquid or fluid can take the form of e.g. an emulsion or a colloidal suspension, without departing from the scope of the invention. It will be understood by those skilled in the art that a wide variety of such components may suitably be included in the fluid water-based compositions and in a wide range of concentrations, the exact preferences depending entirely on the type of product to be constituted by the fluid water-based composition.

The fluid water-based compositions can comprise one or more non-colloidal particulate materials distinctive from the particulate cellulose material, i.e. not including the particulate cellulose material, that are suspended in the aqueous liquid or fluid. These materials are collectively referred to herein as the "non-colloidal particle fraction". As will be understood by those skilled in the art, the term "non-colloidal" refers to dimensional properties and serves to distinguish the respective particles from "colloidal" particles. For the purposes of the present invention, the term "colloidal" is understood to characterize particles as having particle size dimensions in the sub-micron range and the term "non-colloidal" is used to characterize particles as having particle size dimensions typically in the >1 micron range.

In one embodiment, the fluid-water based compositions comprise a non-colloidal suspended particle fraction characterized in that the particles contained in said non-colloidal particle fraction have a particle size, as measured using laser diffraction spectroscopy, using e.g. a Malvern Mastersizer apparatus, of above 1 μm. In this context, "particle size" means that the longest linear dimension of a particle has a value as defined. Those of skill in the art will understand that suitable techniques to measure particle size are available.

In one embodiment, particles within the non-colloidal particle fraction have a size of above 5 μm, more preferably above 10 μm.

In another preferred embodiment of the invention, the non-colloidal particle fraction comprises particles having a volume weighted average major diameter within the range of from 1 μm to 10,000 μm, preferably from 5 μm to 5000 μm, preferably from 10 μm to 2500, most preferably from 20 μm to 1000 μm.

In a preferred embodiment said non-colloidal particle fraction is suspended homogeneously or substantially homogeneously in the aqueous medium.

In one embodiment, the fluid water-based composition comprises a non-colloidal suspended particle fraction at a level of from 0.05 to 80% (w/w), preferably from 0.1 to 50% (w/w), more preferably from 1 to 25% (w/w).

In a preferred embodiment of the invention, the non-colloidal suspended particle fraction comprises particles having a density of from 700 kg/m$^3$ to 4,260 kg/m$^3$, preferably from 800 kg/m$^3$ to 1,200 kg/m$^3$, preferably from 900 kg/m$^3$ to 1,100 kg/m$^3$, preferably from 940 kg/m$^3$ to 1,050 kg/m$^3$, preferably from 970 kg/m$^3$ to 1,047 kg/m$^3$, preferably from and 990 kg/m$^3$ to 1,040 kg/m$^3$ at 25° C.

The fluid water-based composition of the present invention is typically capable of maintaining the non-colloidal particles in suspension for 4 weeks at 25° C. A freshly made composition of the present invention is considered to be stable if less than 10%, preferably less than 5% and more preferably less than 1% by weight of the non-colloidal suspended particles settle to the bottom of a container holding the fluid water-based composition after 4 weeks of static storage.

In an embodiment of the invention, the densities of the non-colloidal suspended particle fraction and the aqueous liquid or fluid differ at least 0.5%, preferably at least 1%, more preferably at least 2.5%, more preferably at least 5%, more preferably at least 10%, still more preferably at least 25%, measured at 25° C. Systems have been stabilized in accordance with the present invention, wherein said difference is as high as 400%.

In an embodiment of the invention, the densities of the non-colloidal suspended particle fraction and the aqueous liquid or fluid differ at least 1 kg/m$^3$, preferably at least 10 kg/m$^3$, more preferably at least 50 kg/m$^3$, more preferably at least 100 kg/m$^3$.

Preferably, the fluid water-based compositions comprise the particulate cellulose material and the non-colloidal suspended particle fraction in a ratio (w/w) within the range of ⅕ to ¹⁄₁₀,₀₀₀, preferably ¹⁄₁₀ to ¹⁄₁₀₀₀.

The nature of the non-colloidal particles can vary widely, depending on the type of product that is constituted by the fluid water-based composition.

For example, in an embodiment of the invention, the fluid water-based composition is a personal care product and the non-colloidal suspended particles may include microbeads that function as a so-called 'scrub' agent. Nowadays, the use of microbeads in personal care is widespread. Microbeads are often used that have a density very close to that of water so that the products remain stable for extended periods of time. This density at the same time makes it extremely difficult to separate microbeads from sewage water and large quantities of these microbeads thus end up in the ecosystem. The present invention provides a solution to this environmental problem by enabling personal care manufacturers to use microbeads having a density that is significantly different from water, without compromising product stability. Hence in a particularly preferred embodiment of the invention, the fluid water-based composition is a personal care product and the non-colloidal suspended particle fraction includes microbeads, typically plastic microbeads, having a density that is at least 1%, at least 2.5%, at least 5%, at least 10%, or at least 20% higher than that of water. In a particularly preferred embodiment of the invention said microbeads comprise or consist of a bio-degradable polymer material. Suitable examples thereof include aliphatic polyesters, such as Polyhydroxyalkanoates (PHAs), like poly-3-hydroxybutyrate (PHB), polyhydroxyvalerate (PHV) and polyhydroxyhexanoate (PHH); Polylactic acid (PLA); Polybutylene succinate (PBS) and polycaprolactone (PCL).

In one embodiment of the invention, the fluid water-based composition is a detergent product or liquid personal care product comprising: (a) an aqueous medium; (b) a surfactant system; and (c) an external structuring agent; wherein said structuring agent comprises the particulate cellulose material as defined in any one of the preceding claims or a liquid detergent product or liquid personal care product according comprising: (a) aqueous medium; (b) 0.1-70% (w/w) of a surfactant system; (c) 0.01-5% (w/w) of external structuring agent. In one embodiment of the invention, the fluid water-based composition is not a detergent product or liquid personal care product comprising: (a) an aqueous medium; (b) a surfactant system; and (c) an external structuring agent; wherein said structuring agent comprises the particulate cellulose material as defined in any one of the preceding claims or a liquid detergent product or liquid personal care product according comprising: (a) aqueous medium; (b) 0.1-70% (w/w) of a surfactant system; (c) 0.01-5% (w/w) of external structuring agent. As used herein, the term "external structuring agent" refers to any material that is added to the liquid surfactant composition with the primary purpose of providing rheological and structuring benefits. An external structuring agent will not in itself provide any significant cleaning benefits. As such, an external structuring agent is distinct from detergent ingredients that also alter or affect the matrix rheology but are added primarily to provide some other benefit, especially to provide significant cleaning benefits, referred to herein as "internal structuring agents". The external structuring agent in accordance with the present invention comprises or consists of the particulate cellulose material of this invention. As will be understood by those skilled in the art, relative and absolute amounts of the particulate cellulose material concern the dry matter weight of the particulate cellulose material, unless indicated otherwise. In one embodiment, the external structuring agent consists entirely of the particulate cellulose material of this invention. Advantageously, the detergent or personal care product comprises at least 0.01% (w/w), more preferably at least 0.05% (w/w), more preferably at least 0.1% (w/w), or at least 0.2% (w/w), or at least 0.3% (w/w), or at least 0.4% (w/w), or at least 0.5% (w/w) of the particulate cellulose material of the invention. Advantageously, the detergent or personal care product comprises up to 5% (w/w), more preferably up to 2.5% (w/w), more preferably up to 2% (w/w), most preferably up to 1.5% (w/w), up to 1.2% (w/w), up to 1.1% (w/w), up to 1.0% (w/w), up to 0.9% (w/w), up to 0.8% (w/w), up to 0.7% (w/w) or up to 0.6% (w/w) of the particulate cellulose material of the invention. In an embodiment of the invention, the liquid detergent product does not contain external structuring agents other than the particulate cellulose material of this invention.

The surfactant system can be a surfactant or combination of surfactants, typically selected from the group consisting of anionic surfactants, cationic surfactants, nonionic surfactants, amphoteric surfactants and zwitterionic surfactants. The content of the surfactant system in the liquid detergent product or liquid personal care product can vary within a wide range. Advantageously, the detergent or personal care product comprises at least 0.1% (w/w), more preferably at least 0.5% (w/w), more preferably at least 1% (w/w), most preferably at least 2.5% (w/w), at least 5% (w/w) or at least 10% (w/w) of surfactant system. Advantageously, the detergent or personal care product comprises up to 70% (w/w), more preferably up to 50% (w/w), more preferably up to 40% (w/w), most preferably up to 35% (w/w), up to 30% (w/w), up to 25% (w/w), up to 20% (w/w) or up to 15% (w/w) of surfactant system. In one embodiment, the detergent or personal care product comprises a weight ratio of surfactant system to external structurant within the range of from 1:1 to 5000:1, preferably from 100:1 to 2000:1, preferably from 500:1 to 1000:1.

The liquid detergent or personal care product can comprise a variety of adjunct ingredients, e.g. to provide further benefits in terms of cleaning power, solubilization, appearance, fragrance, etc. In one embodiment, the detergent or personal care product preferably comprises at least 0.01% (w/w), at least 0.025% (w/w), at least 0.05% (w/w), at least 0.1% (w/w), at least 0.25% (w/w), at least 0.5% (w/w), at least 1% (w/w), at least 2% (w/w), at least 3% (w/w), at least 4% (w/w) or at least 5% (w/w) of adjunct ingredients. In one embodiment, the detergent or personal care product comprises up to 25% (w/w), up to 20% (w/w), up to 15% (w/w), up to 12.5% (w/w), up to 10% (w/w), up to 9% (w/w), up to 8% (w/w), up to 7% (w/w), up to 6% (w/w), or up to 5% (w/w) of adjunct ingredients.

The detergent or personal care product may include electrolytes as adjunct ingredient, in particular water soluble dissociable, inorganic salts such as, for example alkali metal or ammonium sulphates, chlorides, nitrates, phosphates, carbonates, silicates, perborates and polyphosphates, and also certain water soluble organic salts which desolubilise or "salt out" surfactants. Typical levels of electrolyte in the detergent or personal care product are up to 10% (w/w), preferably from 0.5 to 5% (w/w), more preferably from 0.75 to 2.5% (w/w), and most preferably from 1 to 2% (w/w). It has been found that the particulate cellulose material is capable of providing the desired structuring benefits in the presence of significant amounts of electrolytes.

Detergent products, such as a laundry detergent, may comprise one or more detersive enzymes which provide cleaning performance and/or fabric care benefits. Examples include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, mannanases, pentosanases, malanases, β-glucanases, arabinosidases, hyaluronidase, chondroitinase, laccase, and known amylases, and combinations thereof. A preferred enzyme combination comprises a cocktail of conventional detersive enzymes like protease, lipase, cutinase and/or cellulase in conjunction with amylase. Enzyme is typically present at a level of up to 5% (w/w), e.g. from 0.0001 to 0.5% (w/w), preferably from 0.001 to 0.1% (w/w). It has been found that the particulate cellulose material is capable of providing the desired structuring benefits also in the presence of the various enzymes mentioned above.

Detergent products, such as a laundry detergent, may comprise one or more bleaching agents. Among those compounds acting as bleaching agents which release $H_2O_2$ in water, sodium percarbonate, sodium perborate tetrahydrate and sodium perborate monohydrate are of particular significance. Bleaching agent is typically present at levels of 1 to 20% (w/w), preferably 2 to 15% (w/w) and in particular 4 to 12% (w/w). It has been found that the particulate cellulose material is capable of providing the desired structuring benefits also in the presence of bleaching agent in significant amounts.

The detergent or personal care product can typically comprise water in an amount of at least 1% (w/w), more preferably at least 5% (w/w), more preferably at least 10% (w/w), more preferably at least 20% (w/w), more preferably at least 25% (w/w), more preferably at least 30% (w/w). Furthermore, in an embodiment, the liquid product of the invention comprises water in an amount of less than 85% (w/w), more preferably less than 75% (w/w), more preferably less than 70% (w/w), more preferably less than 60% (w/w), more preferably less than 50% (w/w), more preferably less than 40% (w/w), more preferably less than 35% (w/w). In one embodiment, the detergent or personal care product is a concentrated formulation comprising as low as 1 to 30% (w/w) water, preferably from 5 to 15% (w/w), preferably from 10 to 14% (w/w). It has been found that the particulate cellulose material is capable of providing the desired structuring benefits at extreme pH values of above above 10, e.g. above 11 or 12, as well as below 3, e.g. below 2 or 1.

In another exemplary embodiment, the fluid water-based composition is a concrete and the non-colloidal suspended particle fraction can include sand, gravel and/or cement grains.

In yet another exemplary embodiment the non-colloidal suspended particles may include solid food particles and the fluid water-based composition is a sauce or dressing.

In yet another exemplary embodiment the fluid water-based composition is a paint or coating and the non-colloidal suspended particles include pigments. In an embodiment of the invention, fluid water-based compositions are provided as defined herein above, with the proviso that if the fluid water-based composition is a paint or a coating, it comprises less than 1% (w/w) of dispersant, preferably less than 0.5% (w/w), more preferably less than 0.1% (w/w). As will be understood the term dispersant does not encompass the particulate cellulose material of this invention and the recited upper limits apply to the combined amount of dispersants, excluding the particulate cellulose material.

In one embodiment of the invention, the fluid water-based composition is a water-borne acrylic paint or coating composition comprising an aqueous medium, a particulate cellulose material as defined herein dispersed in said aqueous medium, and an acrylic component. In one embodiment of the invention, the fluid water-based composition is not a water-borne acrylic paint or coating composition comprising an aqueous medium, a particulate cellulose material as defined herein dispersed in said aqueous medium, and an acrylic component.

In another embodiment, the fluid water-based composition is a textured paint or plaster composition. Such textured paint or plaster compositions typically comprise (non-colloidal) particles, such as quartz particles. Conferring the proper structuring properties to such compositions is a particular challenge. The present inventors established that the particulate cellulose material of this invention is particularly suitable for application in textured paints and plasters, to which they confer increased resistance to roller spattering at remarkably low levels. This confers the particular advantage that roller spattering can be prevented without having to thicken the paint or plaster to such an extent that it will interfere with the resulting texture, e.g. by smoothening of the edges/transitions of the particles. Hence, in an embodiment of the invention a fluid water-based paint or plaster composition is provided comprising the particulate cellulose material as defined herein as well as non-colloidal particles, preferably quartz particles, clay and/or starch.

In yet another exemplary embodiment the fluid water-based composition is a well drilling fluid and the non-colloidal suspended particles typically include weighting agents, such as barite, dolomite and calcium carbonate. In well drilling the capability of suspending cuttings is also particularly relevant. Hence in an embodiment of the invention, the fluid water-based composition is a well drilling fluid and the particulate cellulose material is used to suspend cuttings during well drilling, which e.g. facilitates removal thereof.

In yet another exemplary embodiment the fluid water-based composition is a fracturing fluid (or fracking fluid) and the non-colloidal suspended particles include proppant articles, which can e.g. include sand or ceramic materials.

Furthermore, embodiments are envisaged where the purpose of the rheological modifications of this invention may be to avoid upward migration or flotation rather of gas bubbles. Hence, additionally or alternatively, the fluid water-based compositions can comprise a plurality of gas bubbles suspended in the aqueous liquid or fluid. Preferably such gas bubbles have a size, as measured using laser diffraction spectroscopy, using e.g. a Malvern Mastersizer apparatus, of above 1 µm. In this context, "particle size" means that the longest linear dimension of a particle has a value as defined. Those of skill in the art will understand that suitable techniques to measure particle size are available. In one embodiment, a plurality of gas bubble having a size of above 5 µm, more preferably above 10 µm, is present in the fluid water-based composition of the invention. In another preferred embodiment of the invention, a plurality of gas bubbles having a volume weighted average major diameter within the range of from 1 µm to 5000 µm, preferably from 5 µm to 2500 µm, preferably from 10 µm to 1000, most preferably from 20 µm to 500 µm, is present in the fluid water-based composition of the invention. In a preferred embodiment said gas bubbles are suspended homogeneously or substantially homogeneously in the aqueous medium.

In one embodiment, the fluid water-based compositions of the invention can comprise additional stabilization agents such as non-polymeric crystalline hydroxyl-functional materials, polymeric structuring agents, and mixtures thereof. It has importantly been found that the particulate cellulose material of the present invention provides sufficient rheological benefits without reliance on additional stabilization agents beyond the particulate cellulose material of this invention. In an embodiment of the invention, the fluid water-based composition does not contain stabilization agents other than the particulate cellulose material of this invention.

In an embodiment of the invention, the fluid water-based compositions comprise less than 0.05% (w/w) of bacterial cellulose. In a preferred embodiment of the invention, the fluid water-based composition comprises less than 0.025% (w/w) of bacterial cellulose, more preferably less than 0.01% (w/w). Most preferably, the fluid water-based composition of the invention is substantially or entirely devoid of bacterial cellulose. Furthermore, in an embodiment of the invention, the fluid water-based composition comprises less than 0.001% (w/w) of citrus fibres. In a preferred embodiment of the invention, the fluid water-based composition comprises less than 0.0005% (w/w) of citrus fibres, more preferably less than 0.00025% (w/w). Most preferably, the fluid water-based composition is substantially or entirely devoid of citrus fibres.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Examples 1

Preparation of Parenchynal Cellulose Composition Containing Particulate Cellulose Material Fresh sugar beet pulp obtained from Suikerunie Dinteloord (NL) was washed in a flotation washer in order to remove sand, pebbles, etc.

In a stirred tank (working volume 70 L) heated with steam), 16.7 kg of washed sugar beet pulp having a solids content of 15% DS (2.5 kg DS in the batch) was introduced and tap water was added to a total volume of 70 L. The mass was heated with steam and, once the temperature reached 50° C., 1200 gram NaOH is added. Heating was continued to reach a final temperature of 95° C. After 45 minutes at 95° C., the mixture was subjected to low shear for 30 minutes (using a Silverson BX with a slitted screen). After a total period of 3 hours at 95° C., low shear was applied again for 60 minutes (using the Silverson BX with an emulsor screen with apertures of 1.5 mm), during which the temperature was kept at approximately 95° C.

Reduction of the particles was done with a Gaulin high pressure homogenizer, operating at 150 bar (first stage; second stage was 0 bar). The mixture was homogenized 6 times. This step was performed at ambient temperature. The mixture had been allowed to cool to ambient temperature before being subjected to the high pressure homogenization treatment.

The homogenized mass was subsequently introduced in a mixing tank and heated to a temperature of 80-85° C., where after a microfiltration step was performed using a ceramic membrane with a pore size of 1.4 µm. The permeate was replaced with demineralized water. As soon as the conductivity of the retentate reached 1 mS/cm, microfiltration was discontinued. The dry solids content was between 0.5 and 1%.

This end-product was subsequently concentrated in a filter bag having pores of 100 µm to reach a dry solids content of 2%.

The material was analyzed using a Malvern Mastersizer, confirming a median (volume-weighted) major dimension of the particles contained within the material of 43.65 µm, with approximately 90% of the material (on the basis of volume) having a particle size of below 100 µm.

Example 2

Preparation of Parenchymal Cellulose Composition Containing Particulate Cellulose Material Fresh sugar beet pulp (320 kg, 24.1% ds) obtained from Suikerunie Dinteloord (NL) was washed in a flotation washer in order to remove sand, pebbles, etc.

The washed sugar beet pulp was transferred to a stirred tank (1000 L) and diluted to a ds concentration of 8% (800 kg). Multifect pectinase FE (Genencor, 139 units/g ds) was added and the suspension was heated to 45° C. After 48 h the suspension was pressed using a membrane filterpress (TEFSA) and the resulting solid material containing the cellulose material was isolated (216 kg 12% ds).

A portion of the resulting cellulose material (20 kg) was introduced in a stirred tank (working volume 70 L) and tap water was added to a total volume of 70 L. The mixture was heated to 95° C. and subjected to low shear for a total period of 3 hours at 95° C. (using a Silverson BX with a slitted screen. Then, low shear was applied for a further 60 minutes (using the Silverson BX with an emulsor screen with apertures of 1.5 mm), during which the temperature was kept at approximately 95° C.

Reduction of the particles was done with a Gaulin high pressure homogenizer, operating at 150 bar (first stage; second stage was 0 bar). The mixture was homogenized 6 times. This step was performed at ambient temperature. The mixture had been allowed to cool to ambient temperature before being subjected to the high pressure homogenization treatment.

The homogenized mass was subsequently introduced in a mixing tank and heated to a temperature of 80-85° C., where after a microfiltration step was performed using a ceramic membrane with a pore size of 1,4 µm. The permeate was replaced with demineralized water. As soon as the conductivity of the retentate reached 1 mS/cm, microfiltration was discontinued. The dry solids content was between 0.5 and 1%.

This end-product was subsequently concentrated in a filter bag having pores of 100 µm to reach a dry solids content of 2%.

The material was analyzed using a Malvern Mastersizer, confirming a median (volume-weighted) major dimension of the particles contained within the material of 51.03 μm, with approximately 90% of the material (on the basis of volume) having a particle size of below 100 μm.

Example 3

Preparation of 'MCF'

A new batch of particulate cellulose material of this invention was produced following the protocol of example 1, except that ensilaged beet pulp was used instead of fresh beet pulp. This time the end-product was concentrated to 5% dry matter content. This product is denominated 'MCF' and was used in all the subsequent experiments, some of which are described here below.

Example 4a

Use of MCF in Liquid Detergent Composition—Surfactant Viscosity Study

An experiment was conducted to evaluate the viscosity of a 0.98 wt % particulate cellulose material with a 10% active solution of various surfactants typically used in liquid laundry detergents and hand dishwashing detergents:
  MCF, as obtained in example 3
  SLES sample was Steol 460 from Stepan
  NaDDBSA neutralized Biosoft S100 from Stepan
Samples of the control and 10% active surfactant were evaluated at t=0 and stored in an oven at 40° C. Every week the samples were stabilized to 25° C. and viscosity determined using a Brookfield Viscometer with speeds and spindle numbers indicated and then maintained at 40° C. until the next viscosity evaluation.

The results of these measurements are summarized in the following table 1. These results show that MCF forms stable mixtures with SLES and Sodium salt of dodecylbenzene sulphonate. Synergetic viscosity build-up takes place with Sodium salt of dodecylbenzene sulphonate. Under these storage conditions a 6 week stability could indicate a 1 year self stability.

TABLE 1

| Viscosity in mPa · s | Spindle | t = 0 | 1 wk | 2 wks | 3 wks | 5 wks | 7.5 wks |
|---|---|---|---|---|---|---|---|
| 0.98 wt % MCF with water (control) | 2@30 rpm | 250 | 255 | 250 | 250* | 250* | 250* |
| 0.98 wt % MCF + 10% SLES (balance water) | 2@30 rpm | 370 | 360 | 360 | 360 | 360 | 360 |
| 0.98 wt % MCF + 10% NaDDBSA (balance water) | 2@12 rpm | 9,700 | 9,700 | 9,500 | 17,000** | 16,800** | 15,800** |

*Some phase separation observed.
**Changed to spindle 3@6 rpm due to increased viscosity.

Example 4b

Use of MCF in Liquid Detergent Composition—Surfactant+Builder Viscosity Study

An experiment was conducted to evaluate the viscosity of a solution of 0.5 wt % MCF with combinations of surfactants and builders typically used in liquid laundry detergents and hand dishwashing detergents:
  Mixtures of 0.5% active MCF+3 to 10% sodium dodecyl benzene sulphonic acid+3 to 7% alcohol ethoxylate+ (optional) 5% citrate or soda ash were tested.

Control sample (0.5% active Betafib in water)=1000 mPa·s

Samples were evaluated at t=0 and stored in a oven at 35° Celsius. At intervals of approx. one week the samples were stabilized to 25° C. and viscosity determined using a Brookfield Viscometer. Samples are maintained at 35° C. until the next viscosity evaluation.

The results of these measurements are summarized in the following table 2. These results show no significant difference in viscosity t=0, 1 week, 2 weeks and 4 weeks (unless indicated otherwise). These results give rise to the following conclusions:
  Higher ratios of Na-DDB SA resulted in more stable product.
  Increasing the ratio of Na-DDBSA resulted in higher viscosity.
  Both soda ash and citrate assisted in increasing the overall viscosity of surfactant blends.
  Both soda ash and citrate assisted in providing better stability for the surfactant blends that were initially unstable (e.g. low Na-DDBSA/high AE).

TABLE 2

| 0.5% active MCF | 10% Na-DDBSA | 7% Na-DDBSA + 3% AE | 5% Na-DDBSA + 5% AE | 3% Na-DDBSA + 7% AE |
|---|---|---|---|---|
| No builder | 1400 mPa · s | 1400 mPa · s | 800 mPa · s | 600 mPa · s |
| 5% soda ash | 3000 mPa · s | 2000 mPa · s | 1400 mPa · s | 1400 mPa · s |
| 5% citrate | 2900 mPa · s | 2000 mPa · s | 2000 mPa · s | 1400* mPa · s |

*initial viscosity 1800 cps
Remark: Some phase separation was seen initially and after 1 week with 5% Na-DDBSA + 5% AE and 3% Na-DDBSA + 7% AE. However, after 2 weeks the mixtures were homogenous.

Example 4c

Use of MCF in Liquid Detergent Composition—Stability of MCF in the Presence of Electrolytes and Builders Samples of MCF were mixed with DI water with the following ratio 6000 ml of DI water with 400 grams of MCF under high shear for 30 minutes. Samples were allowed to stabilize for 2 hours and were then mixed under low sheer for 15 minutes. The solutions would represent a 6.26% solution of MCF, or 0.9375% on a dry basis at 15% w/w of dry matter.

Samples were challenged for accelerated stability by storing in oven at 35 C, temperature for measuring viscosity were measured at 25 C by placing then in a water bath for a couple of hours until this temperature was reached.

The following electrolytes/builders were studies at the following concentrations:

Sodium Citrate, Sodium sulphate, Sodium Metasilicate Pentabead, Sodium carbonate (soda ash dense), Sodium Chloride, Citric acid, Magnesium Sulphate.

% 1.0%, 2.0%, 5.0%

Control: Viscosity without electrolytes 1,800—this viscosity has remained very constant at 1,800 cps.

The results of these measurements are summarized in the following tables 3 and 4 (measurements in mPa·s measured using a Brookfield Viscometer, all measurements are at 25 C and measured in mPa·s). These results give rise to the following conclusions:

The addition of electrolytes/builders increases the viscosity of the MCF.

The results indicate that viscosity of the MCF is not negatively affected by the level of electrolyte/builder. This is very different to most structurants.

An important observation noted is that in no samples were any phase separation even after 6 weeks of oven storage at 35 Celcius. At 6 weeks there was slight changes in viscosity but nothing that would indicate a trend towards significant viscosity loss or significant viscosity gain—generally indicating that MCF is relatively stable to the electrolyte/builders examined.

The results are very interesting in that they demonstrate MCF is remarkably stable in a variety of electrolyte/builder systems—which are very different chemically.

TABLE 3

After 24 hours using spindle 3 at 30 rpm

| Chemical | 0.1% | 1.0% | 2.0% | 5.0% |
|---|---|---|---|---|
| Sodium Citrate | 2,600 | 2,600 | 2,800 | 3,200 |
| Sodium metasilicate | 2,400 | 2,200 | 2,000 | 2,400 |
| Magnesium Sulphate | 2,000 | 2,200 | sample issue | 2,200 |
| Sodium chloride | 2,800 | 2,000 | 2,800 | 2,800 |
| Citric acid | 2,200 | 2,400 | 2,200 | 2,200 |
| Sodium sulphate | 2,800 | 2,800 | 2,800 | 2,800 |
| Sodium carbonate | 2,400 | 2,400 | 2,600 | 2,400 |

TABLE 4

After 6 weeks using spindle 3 at 30 rpm

| Chemical | 0.1% | 1.0% | 2.0% | 5.0% |
|---|---|---|---|---|
| Sodium Citrate | 2,800 | 2,800 | 2,800 | 3,000 |
| Sodium metasilicate | 2,600 | 2,600 | 2,400 | 2,400 |
| Magnesium Sulphate | 2,200 | 2,200 | Sample issue | 2,200 |
| Sodium chloride | 2,600 | 2,400 | 2,800 | 2,600 |
| Citric acid | 2,400 | 2,400 | 2,400 | 2,400 |
| Sodium sulphate | 2,600 | 2,600 | 2,600 | 2,800 |
| Sodium carbonate | 2,600 | 2,200 | 2,200 | 2,400 |

Example 5

Stress-Shear Rate Profile

FIG. 1a shows the stress vs. shear rate profile of a 0.5% (w/w) MCF in water system. The measurements were made using using a Haake model RV550 viscometer (rotor MV1), at 1 to 1000 s$^{-1}$ and conducted at 25° C. As can be inferred from this profile the slope is >>0, which is indicative of sufficient flow stability.

Figure 1B:
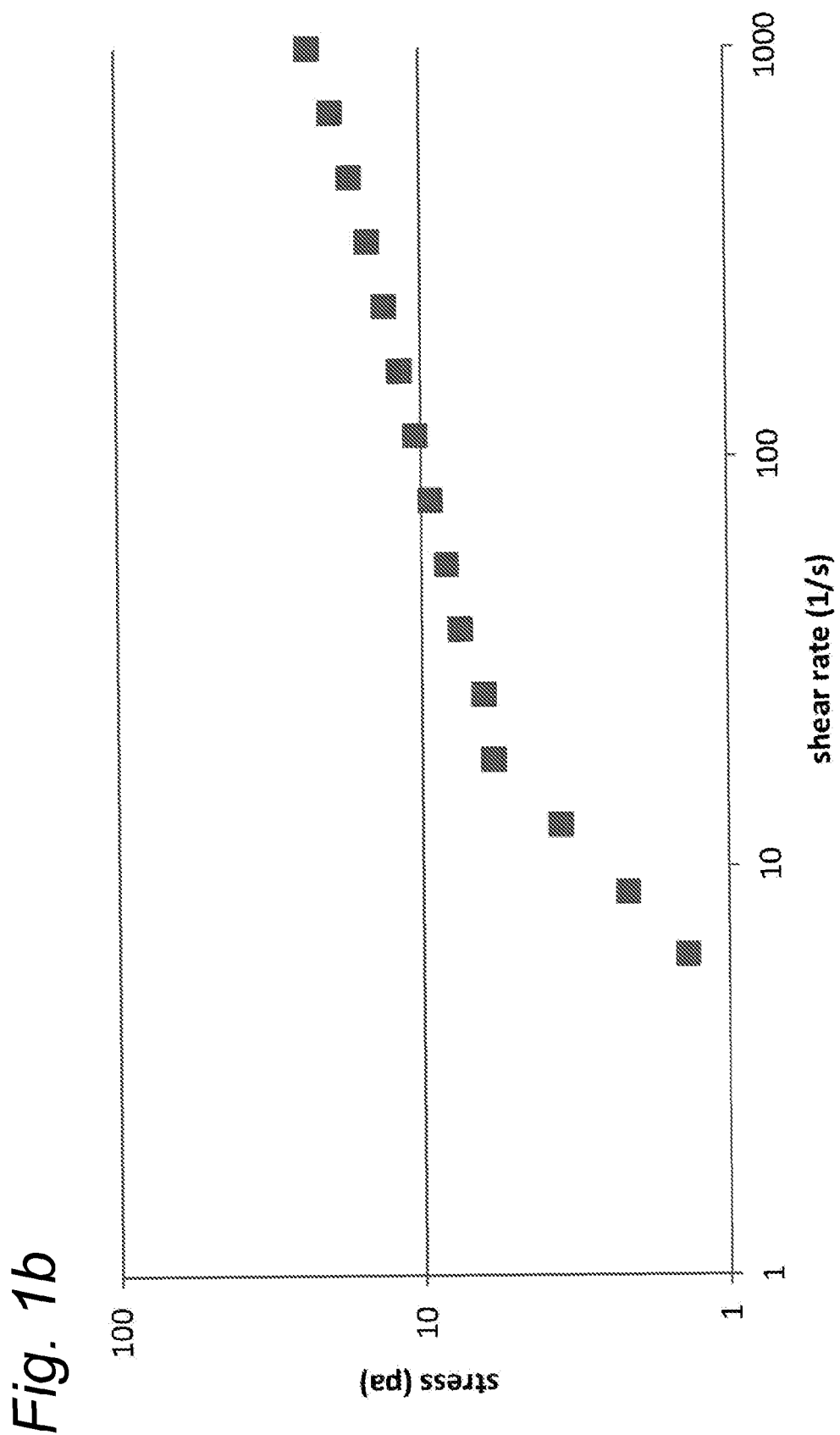
FIG. 1b shows the stress vs. shear rate profile of a 1.0% (w/w) MCF in water system.

FIG. 1b shows the stress vs. shear rate profile of a 1.0% (w/w) MCF in water system. The measurements were made using using a Haake model RV550 viscometer (rotor MV), at 1 to 1000 s$^{-1}$ and conducted at 25° C. As can be inferred from this profile the slope is >>0, which is indicative of sufficient flow stability.

Example 6

Effect of pH on Viscosity

Figure 2:
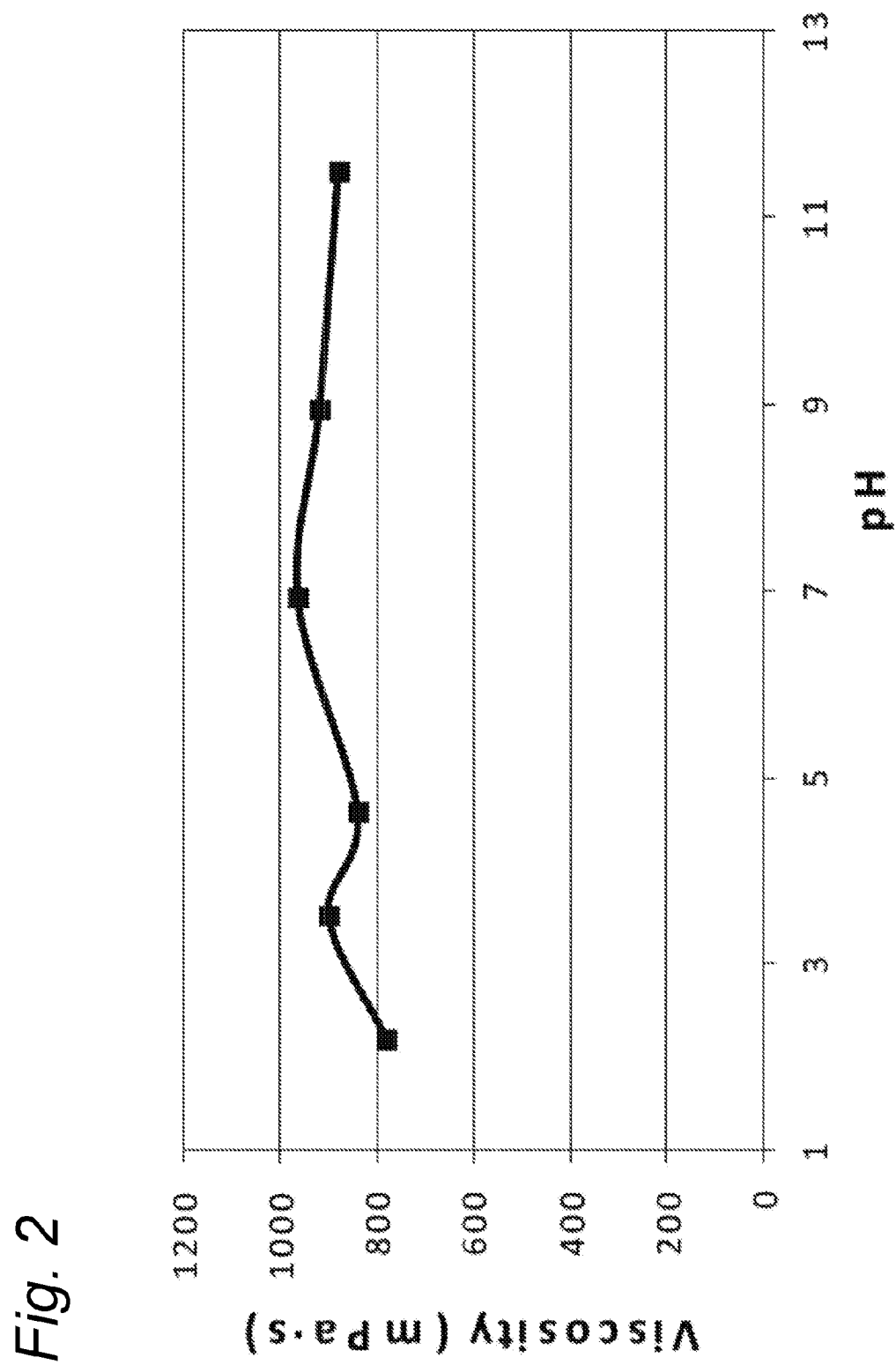
FIG. 2 shows the viscosity vs. pH profile of a 0.6% (w/w) MCF in water system, the pH of which was adjusted using NaOH and HCl.

FIG. 2 shows the viscosity vs. pH profile of a 0.6% (w/w) MCF in water system, the pH of which was adjusted using NaOH and HCl. The measurements were made using a Haake model RV550 viscometer (rotor MV1), at 1 to 1000 s$^{-1}$ and conducted at 25° C. As can be inferred from this profile the viscosity is hardly affected by the pH value of the system.

Example 7

Effect of HCl on Stability

Figure 3A:
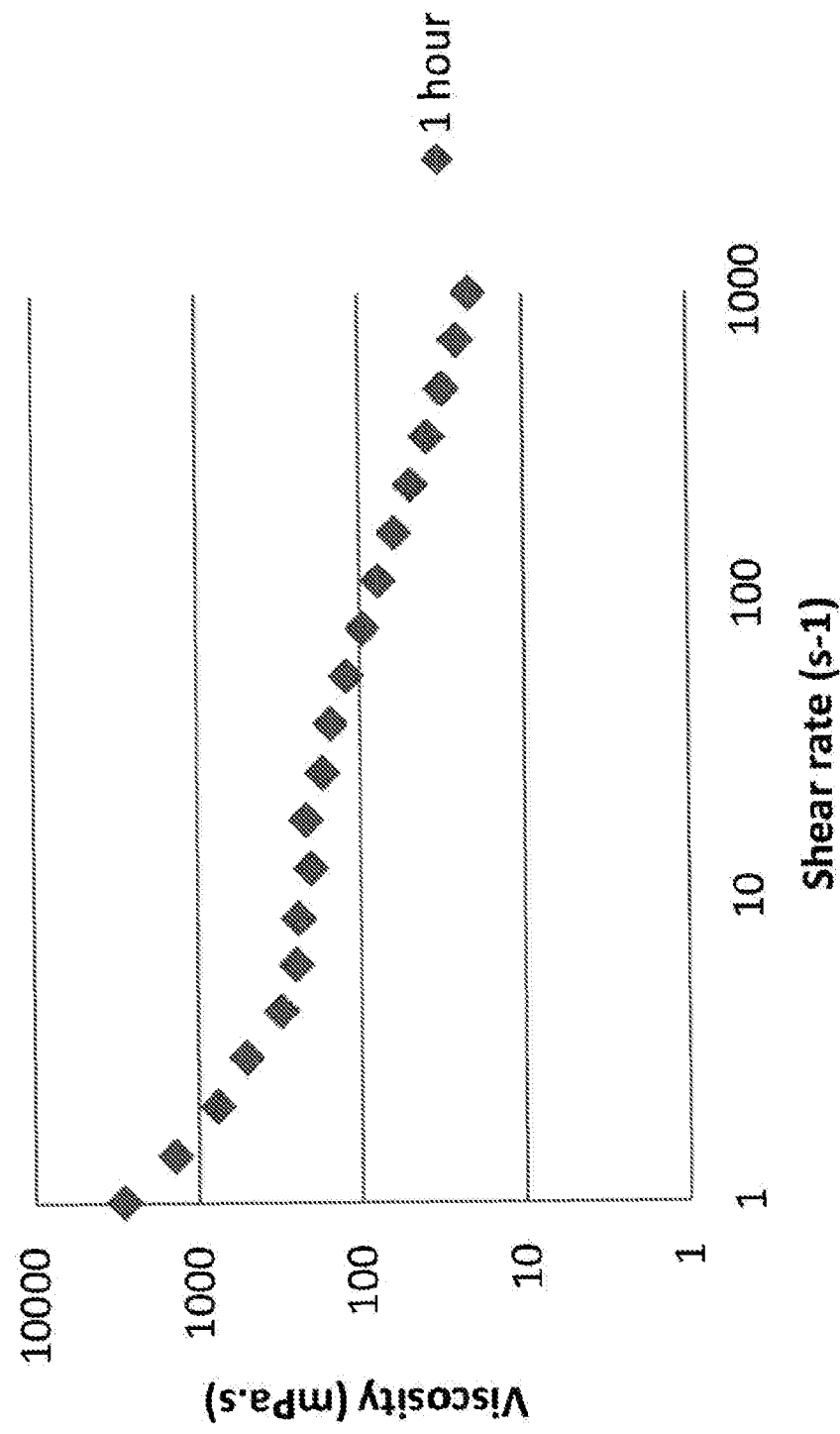
FIGS. 3a, 3b and 3c show the shear rate vs. viscosity profile of a 1% (w/w) MCF in water system, containing 9% (w/w) HCl, after 1 hour, 24 hours and 48 hours respectively.
Figure 3B:
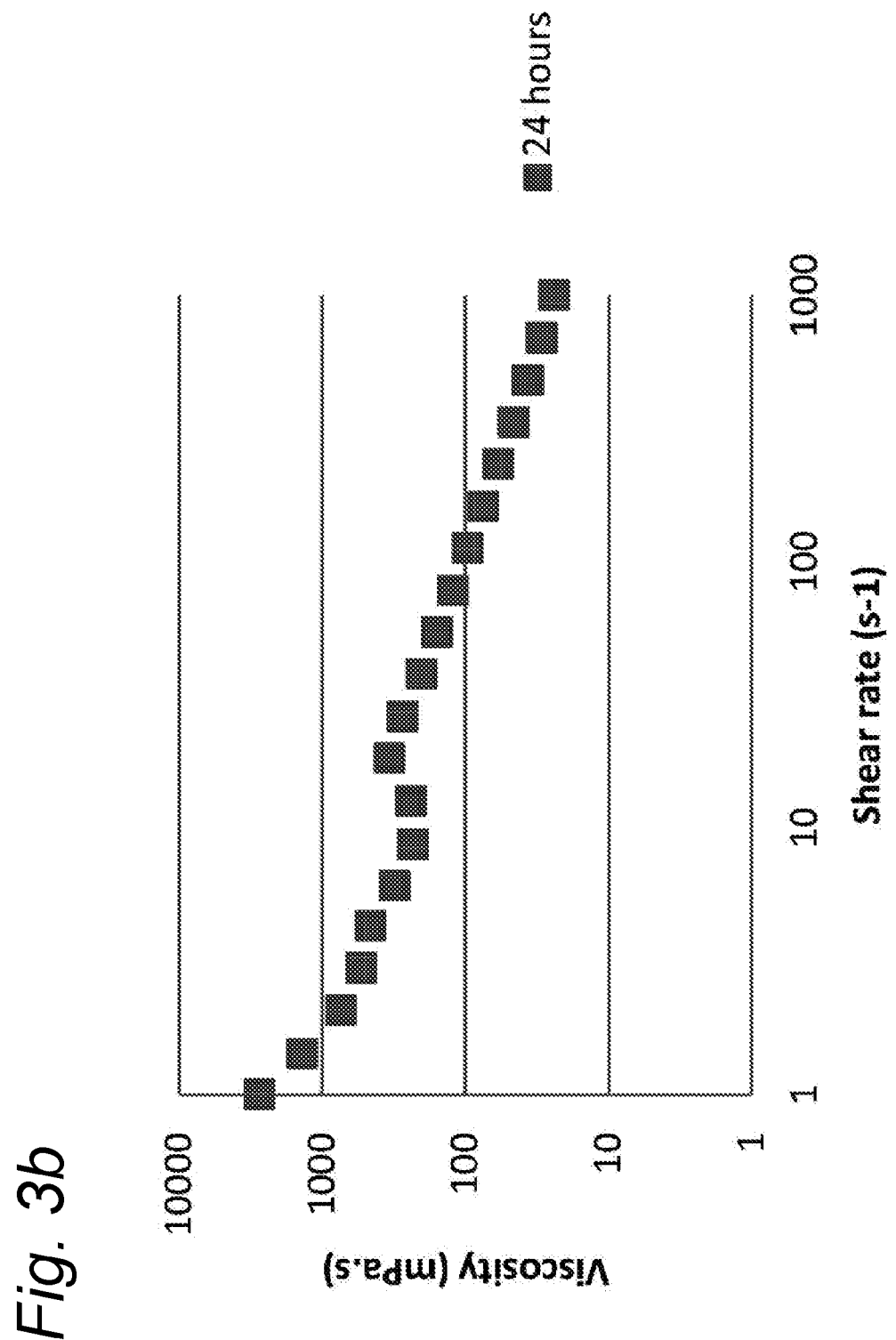
Figure 3C:
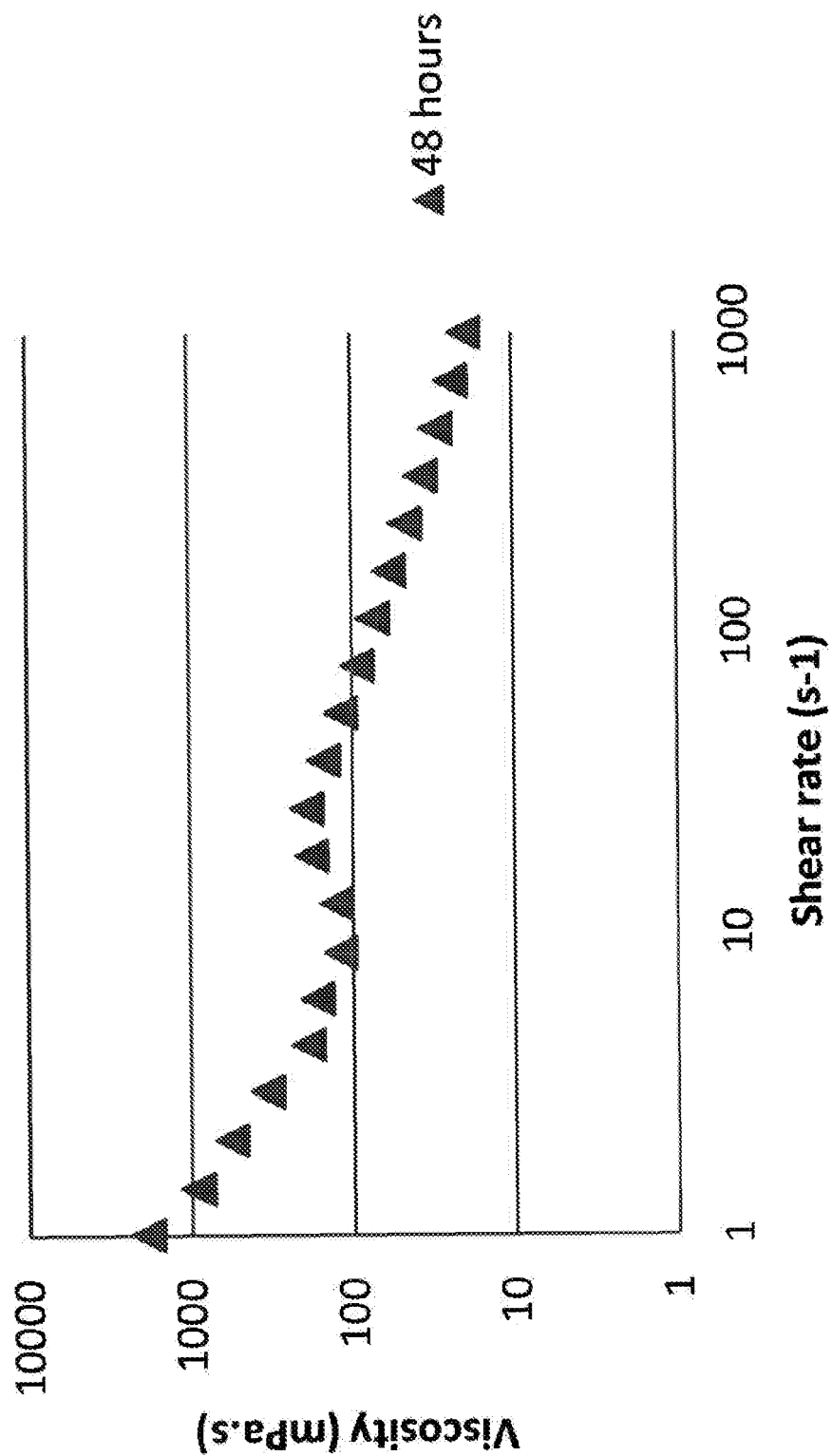

FIGS. 3a, 3b and 3c show the shear rate vs. viscosity profile of a 1% (w/w) MCF in water system, containing 9% (w/w) HCl, after 1 hour, 24 hours and 48 hours respectively. The measurements were made using a Haake model RV550 viscometer (rotor MV1), at 1 to 1000 s$^{-1}$ and conducted at 25° C. As can be inferred from these figures the profile did not substantially change over the 48 hour test period. This is indicative of the stability of the structuring agent of the present invention in extremely acidic systems.

Example 8

Effect of CaCO$_3$ Particles on Viscosity

Figure 4:
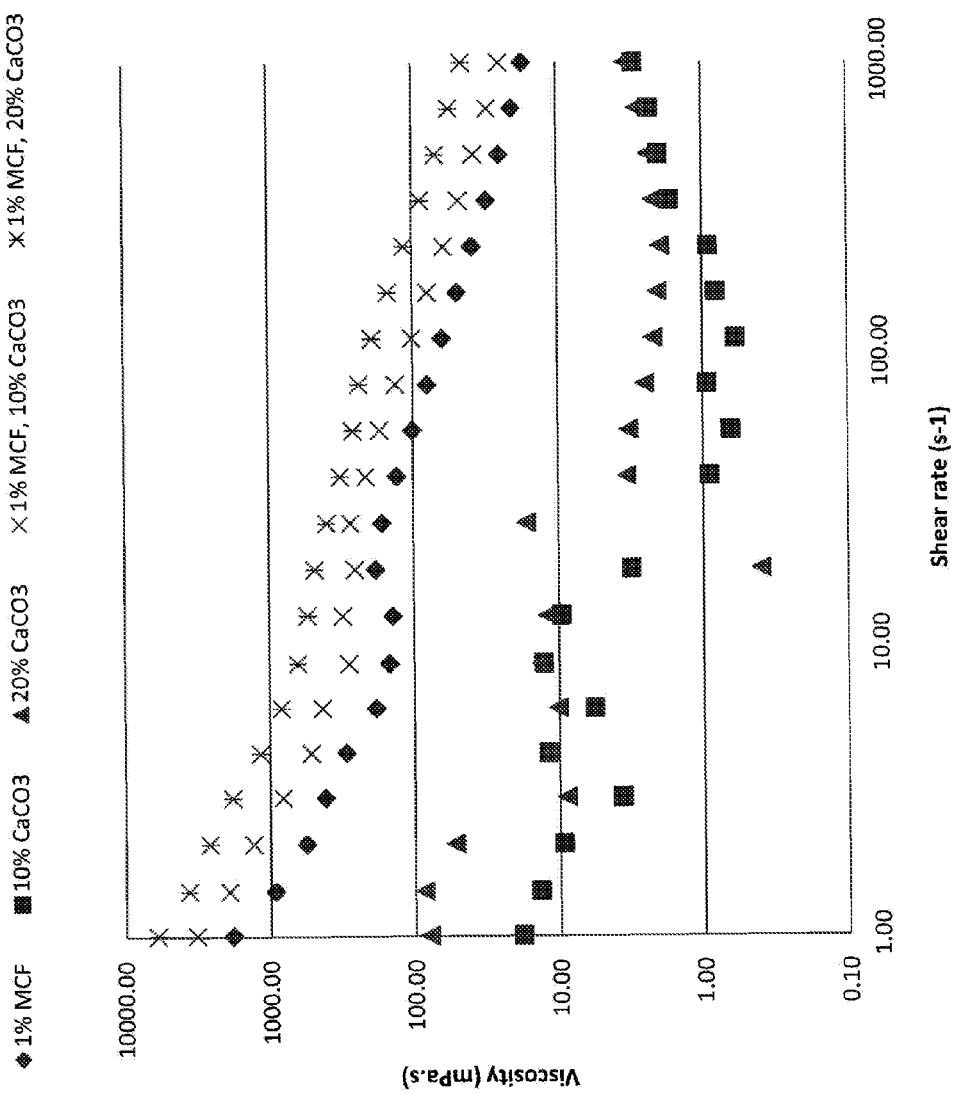
FIG. 4 shows the shear rate vs. viscosity profile of the following MCF structured systems and control samples:
 1% (w/w) MCF in tap water
 10% (w/w) $CaCO_3$ in tap water
 20% (w/w) $CaCO_3$ in tap water
 1% (w/w) MCF+10% (w/w) $CaCO_3$ in tap water
 1% (w/w) MCF+20% (w/w) $CaCO_3$ in tap water

FIG. 4 shows the shear rate vs. viscosity profile of the following MCF structured systems and control samples:
1% (w/w) MCF in tap water
10% (w/w) CaCO$_3$ in tap water
20% (w/w) CaCO$_3$ in tap water
1% (w/w) MCF+10% (w/w) CaCO$_3$ in tap water
1% (w/w) MCF+20% (w/w) CaCO$_3$ in tap water The measurements were made using a Haake model RV550 viscometer (rotor MV1), at 1 to 1000 s$^{-1}$ and conducted at 25° C. As can be inferred from this figure, the presence of particles of non-soluble material (CaCO$_3$) does not substantially change the profile. The presence of such particles slightly increases the viscosity of the system.

Example 9

Effect of Bleaching on Viscosity

Figure 5:
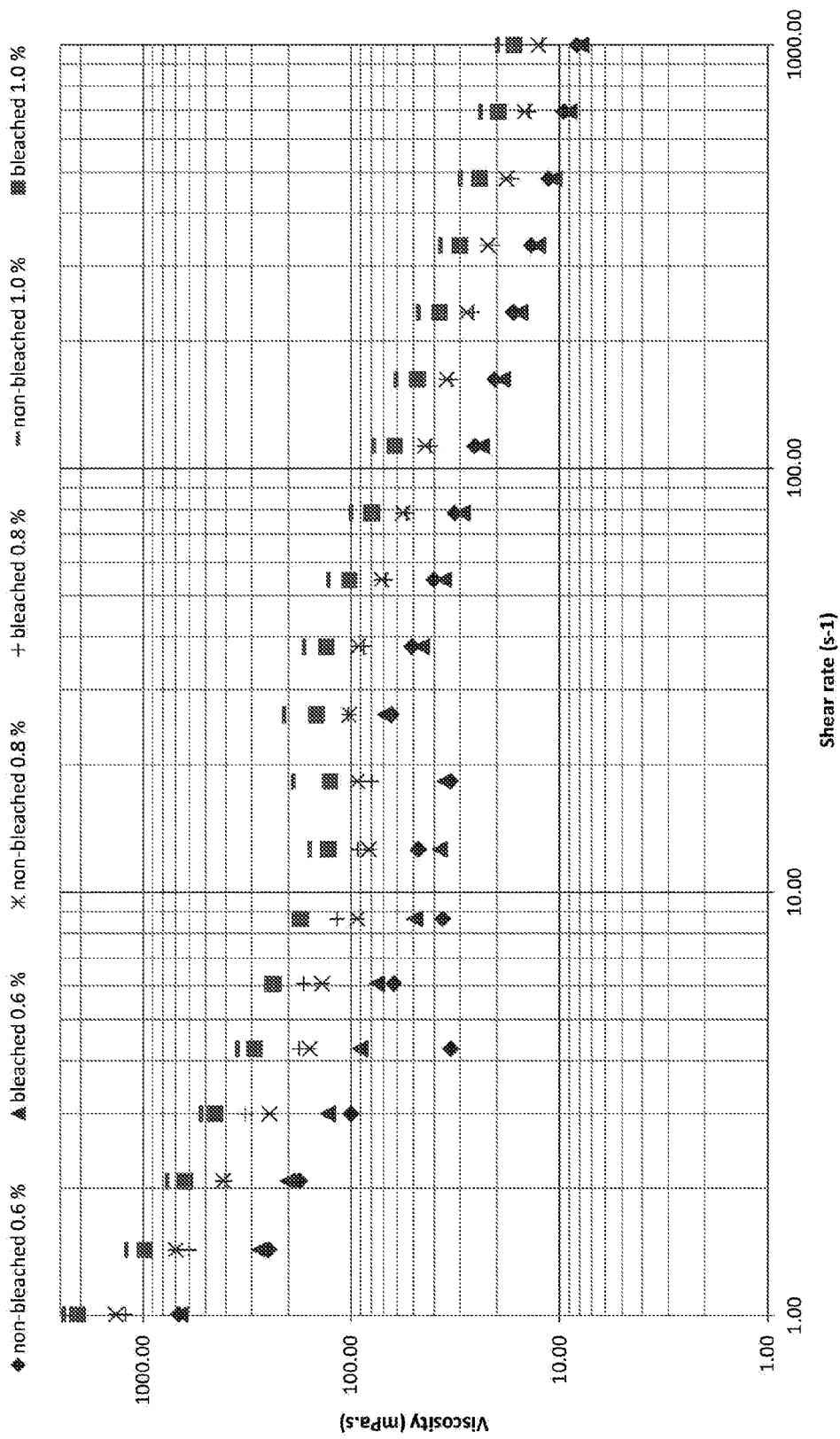
FIG. 5 shows the shear rate vs. viscosity profile of the following MCF structured systems and control samples:
 0.6% (w/w) MCF in tap water
 0.6% (w/w) bleached MCF in tap water
 0.8% (w/w) MCF in tap water
 0.8% (w/w) bleached MCF in tap water
 1.0% (w/w) MCF in tap water
 1.0% (w/w) bleached MCF in tap water

An amount of MCF was subjected to treatment with sodium silicate, diethylene triamine pentaacetic acid (DTPA) and H$_2$O$_2$ (pH adjustment with NaOH and H$_2$SO$_4$), which resulted (after washing) in a product with improved visual appearance. FIG. 5 shows the shear rate vs. viscosity profile of the following MCF structured systems and control samples:
0.6% (w/w) MCF in tap water
0.6% (w/w) bleached MCF in tap water
0.8% (w/w) MCF in tap water
0.8% (w/w) bleached MCF in tap water
1.0% (w/w) MCF in tap water
1.0% (w/w) bleached MCF in tap water The measurements were made using a Haake model RV550 viscometer (rotor MV1), at 1 to 1000 s$^{-1}$ and conducted at 25° C. As can be inferred from this figure, applying a bleaching step to improve the visual appearance of the structuring agent of the invention does not substantially change the profile.

Example 10

Use of Particulate Cellulose Material in Self Compacting Concrete

In this example, the influence of MCF on self-compacting concrete (SCC) is tested. Unlike 'normal' concrete, SCC is flowable and has the ability to spread into place. The influence of micro cellulose on SCC has been examined before. Micro cellulose has been shown to decrease workability by the viscosity increase.

To examine the influence of MCF on cement hydration, a series of tests was conducted on a SCC cement paste with a water to cement ratio of 0.4. Cement paste is a mixture of water and cement. There were three series of samples, each with a different amount of micro cellulose fibres. The first one was a control group without any cellulose, the second one contained 0.125% MCF. The percent values refer to the weight of the water. The hydration of the samples was stopped at 7 days by grinding with mortar and pestle with acetone. The powder was then kept in a dry environment. A viscosity test, a cone test and a segregation test was conducted. The SCC mixture used is shown in the following table:

|  | gravel |  | Sand |  |  | water | cement | LP | SP |
|---|---|---|---|---|---|---|---|---|---|
| Size (mm) | 4-8 | 2-4 | 1-2 | 0.5-1 | 0.25-0.5 | 0.125-0.25 |  |  |  |
| Weight (kg) | 531.2 | 121.4 | 106.2 | 212.4 | 349 | 197.2 | 175 | 380.2 | 190 | 4.2 |

SCC mixture for 1 m$^3$ concrete without cellulose,
SP: superplacticizer Glenium 51 con. 35%,
LP: limestone powder The cement (CEM I 42.5N) and the superplasticizer (Glenium 51 con 0.35%) are according to DIN EN 197-1 and DIN EN 934-2 respectively.

Viscosity

Test A BML viscometer (ConTec BML Viscometer) measures the torque needed to rotate a ripped bucket filled with concrete around a ripped test cylinder. The cylinder and the bucket are coaxial. The test cylinder does not move and measures the torque. The bucket is the moving part; it is placed and end-matched onto a rotating disc that can move at different speeds. By measuring the torque at different rotation speeds, the shear stress and the plastic shear viscosity can be calculated.

The viscosity tests show an increase in both shear stress and plastic shear viscosity with MCF, as can be inferred from the following table:

|  | shear stress [Pa] | plastic shear viscosity [Pas] |
|---|---|---|
| control | 2 | 30 |
| 0.125% | 18 | 89 |

Cone Test

To verify that the used concrete mixture is actually SCC, a cone test was conducted. The metal cones have the shape of a frustum and are placed on a wooden board which is slightly oiled. The procedure is to fill the cone with concrete and then lift the cone. The test was done according to DIN EN 12350-2 with the following alterations: the wooden board was slightly oiled and the concrete was not compacted with a beater since it is self compacting concrete. The cone used was according to the norm with a basis diameter of 200 mm, a top diameter of 100 mm and 300 mm height. Furthermore, a second, smaller cone was used with a basis diameter of 100 mm, a top diameter of 70 mm and a height of 60 mm. Two series of tests were done: One immediately after mixing and one 30 min later.

The tests result in a slump value. It is the difference between the height of the metal cone and the height of the concrete cone after removing the metal cone. Due to the fact that SCC was used, also the flow could be measured as the averaged diameter of the circle that the concrete spreads into according to DIN EN 12350-8.

In the control group, the concrete spreads completely immediately after mixing. Therefore the slump is the maximum value of 60 mm for the small and 300 mm for the big cone. After 30 minutes, a small decrease in flow can be measured as well as a small decrease in the slum value and a lot of bleeding was visible. The results for the control group are summarized in the following table.

|  | Small cone | | Big cone | |
|---|---|---|---|---|
|  | t = 0 min | t = 30 min | t = 0 min | t = 30 min |
| Diameter (mm) | 240 | 230 | 750 | 750 |
| Slump (mm) | 60 | 30 | 300 | 240 |

With 0.125% MCF and the big cone, the mixture spreads to 600 mm and has a slump of 275 mm immediately after mixing. The small cone shows a flow of 170 mm and a slump of 40 mm. After 30 min, the results are almost the same. The results for the 0.125% MCF group are summarized in the following table.

|  | Small cone | | Big cone | |
|---|---|---|---|---|
|  | t = 0 min | t = 30 min | t = 0 min | t = 30 min |
| Diameter (mm) | 240 | 230 | 750 | 750 |
| Slump (mm) | 60 | 30 | 300 | 240 |

Segregation

Figure 6A:
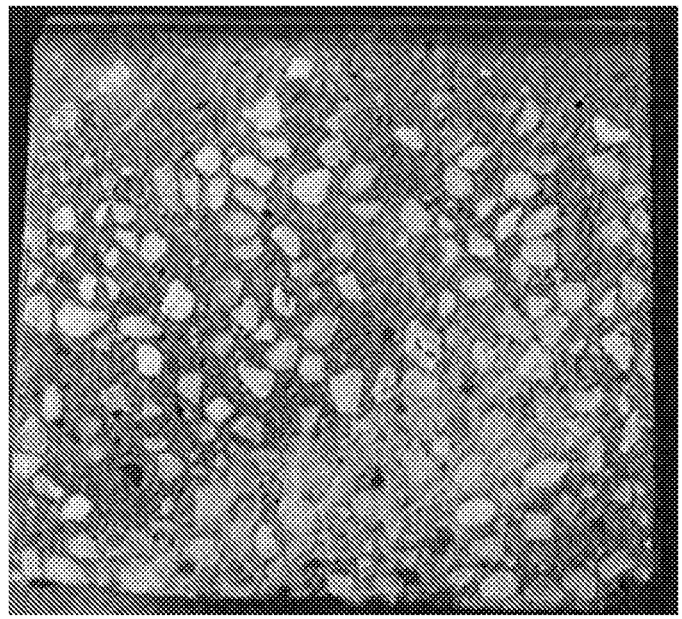
FIG. 6a shows the MCF-free control mixture shows segregation in the upper part of the block.
Figure 6B:
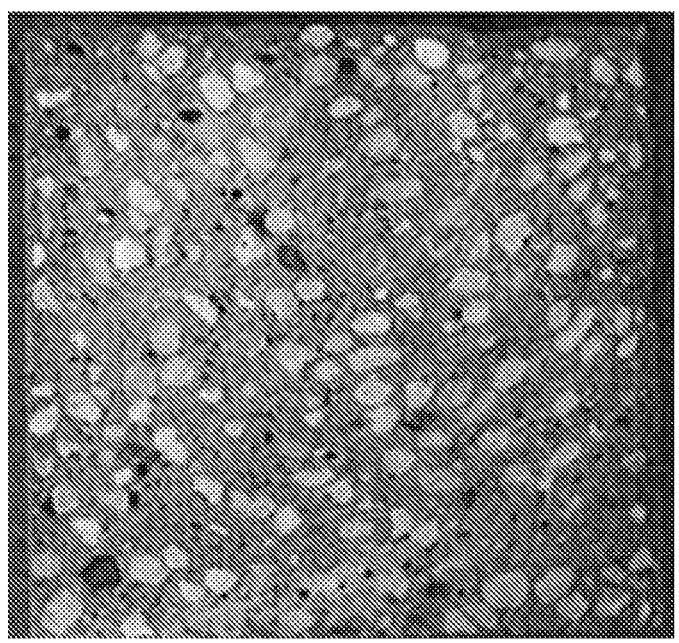
FIG. 6b depicts how segregation is not visible in the 0.125% MCF mixture.

For the segregation test, a cube with an edge length of 15 cm was casted. After hardening, the cube was vertically cut in half and the segregation was evaluated visually. The MCF-free control mixture shows segregation in the upper part of the block (FIG. 6A). Coarse material is concentrated in the lower part of the block. Segregation is not visible in the 0.125% MCF mixture (FIG. 6B). All ingredients are evenly distributed.

Example 11

Preparation of Parenchymal Cellulose Composition Containing Particulate Cellulose Material 132 kg of ensilaged sugar beet pulp is washed in a flotation washing machine to remove all non sugar beet pulp items (sand, stones, wood, plastic, etc.). After washing, the sugar beet pulp is diluted with the same volume of water (132 kg) and heated up to 40° C. under continues slow mixing. At this temperature NaOH pellets are added to reach a molarity of 0.5M (5.3 kg NaOH pellets). Then the temperature is increased to 95° C. The silverson FX is switched on and the mixture is sheared during the complete reaction time of 60 minutes to reach a smooth texture. Then the mixture is cooled down to 80° C. and pumped into an chamber filter press to remove most of the water including a part of the proteins, hemicelllulose and pectins. The filtrate is pumped to the sewage and the pressed cake is diluted with water of ambient temperature to a dry matter concentration around 1-2%. Then to this suspension sulfuric acid is added to reach a pH below 2 (about 8 liters of 25% sulfuric acid). After acidifying, the material is mixed with the Silverson FX during 15 minutes. After complete mixing the suspension is pumped to a high pressure Gaulin Homogeniser. The homogenizer is set on 150 bar (one stage) and the material is run through the homogenizer until a particle size (D[4,3]) of approximately 65 µm is reached. Then the suspension is pumped to the Chamber filter press. In the press the material is pressed to a dry matter content of 25%. The pressed cakes are then grinded into powder-like material and, which is packaged in an air-tight package.

Example 12

Recovery of Initial Viscosity after Shear

Figure 7A:
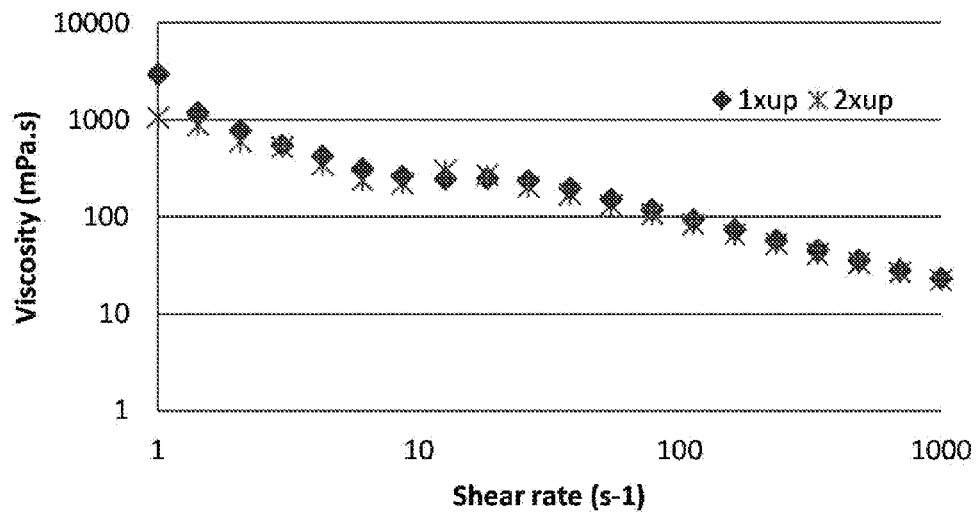
FIG. 7a shows the up-curves of the two cycles.
Figure 7B:
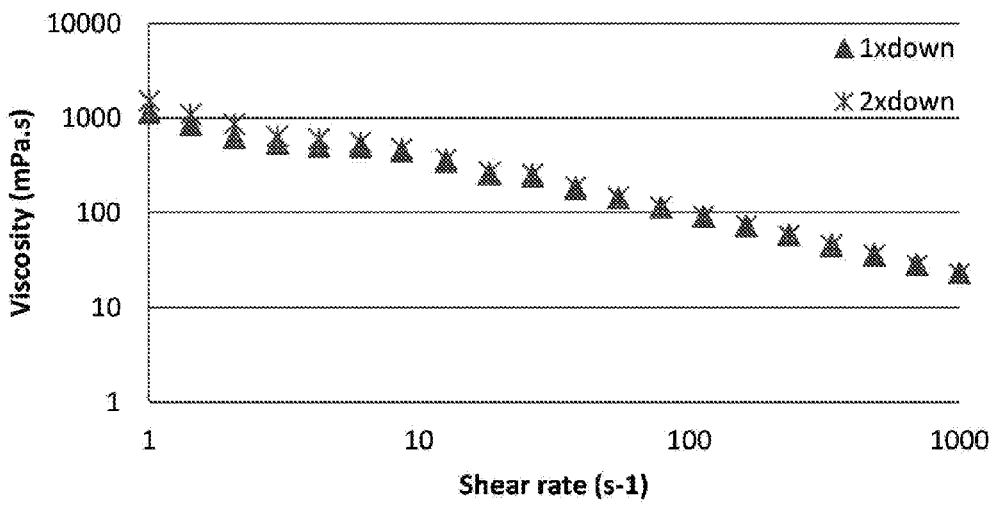
FIG. 7b shows the "down curves" of the two cycles.

A fluid composition comprising 1% (w/v), based on dry weight, of the material produced in accordance with example 11 in water, was subjected to a standard viscosity testing protocol as described herein elsewhere. This time the "up curve" as well as the "down curve" was recorded. This procedure was performed twice. The results are shown in FIG. 7A, showing the up-curves of the two cycles, and 7B, showing the "down curves" of the two cycles. As can be inferred from these figures the "up curve" and "down curve" in each cycle are very close to one another and the curves of the $1^{st}$ and $2^{nd}$ cycle (substantially) coincide. These findings indicate that the aqueous fluid structured with the material of example 11 is capable of quick and complete recovery of initial viscosity after shearing, properties that are also apparent from simple qualitative assessment.

Example 13

Preparation of Parenchymal Cellulose Composition Containing Particulate Cellulose Material 180 kg of ensilaged sugar beet pulp is washed in a flotation washer to remove all non sugar beet items. Then the washed sugar beet pulp is diluted to 600 kg with water. This suspension is slowly mixed and meanwhile sulfuric acid is added to reach a pH of 1,5 (8 liter 25% sulfuric acid). Then the suspension is heated up to 85° C. and mixed during 60 minutes with the Silverson FX. The suspension is then pumped to the Chamber filter press. The filtrate is kept separate to purify and solidify the pectines. The pressed cake is suspended in water under mixing to reach a dry matter of 3-5% dm. Then this suspension is heated up to 40° C. and NaOH pellets are added up to 0.5M (about 5 kg NaOH pellets). Then it is heated up to 95° C. for one hour under continuous mixing. Then the mixture is cooled down to 80° C. and pressed in the chamber filter press. The pressed cakes are then diluted with water to 1% DM under mixing and pumped into the homogenizer. The homogenizer is set on 150 bar (one stage) and the material is run through the homogenizer until a particle size (D[4,3]) of approximately 65 µm is reached. Then the mixture is pumped to the chamber filter press where the DM is increased to 25%. The pressed cakes are grinded into powder-like material. The product accordingly obtained had a more attractive visual appearance than the product obtained in accordance with example 11, in particular in that it appeared significantly whiter.

The invention claimed is:

1. A method for:
   (i) imparting shear thinning behavior in a fluid water-based composition;
   (ii) imparting a high zero-shear viscosity in a fluid water-based composition, said high zero-shear viscosity being characterized by value above $10^5$ mPa·s;
   (iii) imparting thixotropic behavior in a fluid water-based composition;
   (iv) imparting a high low-shear viscosity in a fluid water-based composition, said high low-shear viscosity being characterized by a value of above $10^5$ mPa·s, at a shear rate within the range of $10^{-6}$-$10^{-2}$ s$^{-1}$;
   (v) imparting a yield stress in a fluid water-based composition, said yield stress being characterized by a value within the range of 0.003 to 5.0 Pa; and/or
   (vi) stabilizing a non-colloidal suspended particle fraction in a fluid water-based composition;
   wherein the fluid water-based composition comprises at least 10% (w/w) of water as well as a non-colloidal suspended particle fraction,
   the method comprising incorporating into the fluid water-based composition:
   (a) a particulate cellulose material comprising, by dry weight, at least 60% cellulose, 0.5-10% pectin and 1-15% hemicellulose, and having a volume-weighted median particle dimension within the range of 25-75 µm as measured by laser light diffractometry; and/or
   (b) a particulate cellulose material obtainable by a method comprising:
      (A) subjecting a parenchymal cell containing vegetable pulp to chemical and/or enzymatic treatment resulting in partial degradation and/or extraction of pectin and hemicellulose; and
      (B) subjecting the material resulting from (A) to a high shear process to yield a particulate material having a volume-weighted median dimension within the range of 25-75 µm, as measured by laser diffractometry.

2. The method according to claim 1, wherein the vegetable pulp is pulp obtained from sugar beet, chicory, beet root, turnip, carrot or potato.

3. The method according to claim 1, wherein the particulate cellulose material has at least 90%, on a volume basis, particles having a diameter less than 120 μm.

4. The method according to claim 3, wherein the particulate cellulose material has at least 90%, on a volume basis, particles having a diameter less than 110 μm.

5. The method according to claim 1, wherein the particulate cellulose material have a morphology comprising a cellulose network structures.

6. The method according to claim 1, wherein the particulate cellulose material comprises less than 10 wt. % of unraveled cellulose nanofibrils.

7. The method according to claim 1, wherein the fluid water-based composition is selected from the group consisting of personal care products, liquid detergent products, alimentary products, concrete, mortar and spray plaster.

8. The method according to claim 1, wherein the particles of said non-colloidal suspended particle fraction have a particle size above 1 μm.

9. A fluid water-based composition, comprising:
(a) at least 10% (w/w) of an aqueous liquid or fluid;
(b) a particulate cellulose material; and
(c) a non-colloidal suspended particle fraction,
wherein the composition is shear thinning and has a viscosity above $10^5$ mPa·s at a shear rate within the range of $10^{-6}$-$10^{-2}$ s$^{-1}$, wherein:
(i) the particulate cellulose material comprises, by dry weight, at least 60% cellulose, 0.5-10% pectin and 1-15% hemicellulose, and has a volume-weighted median particle dimension between 25-75 μm, as measured by laser light diffractometry; and/or
(ii) the particulate cellulose material is obtainable by a method, comprising:
(A) subjecting a parenchymal cell containing vegetable pulp to chemical and/or enzymatic treatment resulting in partial degradation and/or extraction of pectin and hemicellulose;
(B) subjecting the material of (A) to a high shear process whereby the particle size of the cellulose material has a volume-weighted median dimension within the range of 25-75 μm, as measured by laser diffractiometry.

10. The method according to claim 9, wherein the particulate cellulose material has a volume-weighted median particle dimension between 35-65 μm, as measured by laser light diffractometry.

11. The fluid water-based composition according to claim 9, wherein the vegetable pulp is pulp obtained from sugar beet, chicory, beet root, turnip, carrot or potato.

12. The fluid water-based composition according to claim 9, wherein the composition has a slope of stress (on y axis, measured in pascals) versus shear rate (on x axis, measured in s$^{-1}$) of 0.05 to 0.75.

13. The fluid water-based composition according to claim 9, wherein the particulate cellulose material has at least 90%, on a volume basis, particles having a diameter less than 120 μm.

14. The fluid water-based composition according to claim 13, wherein the particulate cellulose material has at least 90%, on a volume basis, particles having a diameter less than 110 μm.

15. The fluid water-based composition according to claim 9, wherein the particulate cellulose material has a morphology comprising cellulose network structures.

16. The fluid water-based composition according to claim 9, wherein the particulate cellulose material comprises less than 10 wt. % of unraveled cellulose nanofibrils.

17. The fluid water-based composition according to claim 9, wherein the fluid water-based composition is selected from the group consisting of personal care products, liquid detergent products, alimentary products, concrete, mortar, and spray plaster.

18. The fluid water-based composition according to claim 9, wherein the particles in the non-colloidal particle fraction have a particle size of above 1 μm.

19. A method of producing a particulate cellulose material, the method comprising:
(a) subjecting ensilaged parenchymal cell comprising sugar beet pulp to chemical and/or enzymatic treatment resulting in partial degradation and/or extraction of pectin and hemicellulose; and
(b) subjecting the material resulting from (a) to a high shear process to yield a particulate material having a volume-weighted median dimension between 25-75 μm, as measured by laser diffractiometry.

\* \* \* \* \*